(12) United States Patent
Nease, Jr. et al.

(10) Patent No.: US 8,799,204 B1
(45) Date of Patent: Aug. 5, 2014

(54) METHODS AND SYSTEMS FOR MEMBER MESSAGING

(75) Inventors: Robert F. Nease, Jr., St. Louis, MO (US); Katherine Harini Sundararaman, St. Louis, MO (US); Heather D. Sundar, Edwardsville, IL (US); Krista Lynn Theby, St. Louis, MO (US); Tina Lynn Bauman Butcher, Indianapolis, IN (US)

(73) Assignee: Express Scripts, Inc., St. Louis, MO (US)

( * ) Notice: Subject to any disclaimer, the term of this patent is extended or adjusted under 35 U.S.C. 154(b) by 329 days.

(21) Appl. No.: 13/331,171

(22) Filed: Dec. 20, 2011

Related U.S. Application Data

(63) Continuation-in-part of application No. 13/066,664, filed on Apr. 19, 2011, now Pat. No. 8,666,926.

(60) Provisional application No. 61/474,191, filed on Apr. 11, 2011, provisional application No. 61/325,743, filed on Apr. 19, 2010.

(51) Int. Cl.
*G06F 17/00* (2006.01)
*G06N 5/02* (2006.01)

(52) U.S. Cl.
USPC .......................................................... 706/50

(58) Field of Classification Search
CPC combination set(s) only.
See application file for complete search history.

(56) References Cited

U.S. PATENT DOCUMENTS

| | | | |
|---|---|---|---|
| 6,468,210 B1 * | 10/2002 | Iliff | 600/300 |
| 6,475,143 B2 * | 11/2002 | Iliff | 600/300 |
| 6,524,241 B2 * | 2/2003 | Iliff | 600/300 |
| 6,527,713 B2 * | 3/2003 | Iliff | 600/300 |
| 6,569,093 B2 * | 5/2003 | Iliff | 600/300 |
| 6,587,829 B1 | 7/2003 | Camarda et al. | |
| 6,730,027 B2 * | 5/2004 | Iliff | 600/300 |
| 6,746,399 B2 * | 6/2004 | Iliff | 600/300 |
| 6,764,447 B2 * | 7/2004 | Iliff | 600/300 |
| 6,767,325 B2 * | 7/2004 | Iliff | 600/300 |
| 6,817,980 B2 * | 11/2004 | Iliff | 600/300 |
| 7,054,706 B2 | 5/2006 | Kempf et al. | |
| 7,389,211 B2 | 6/2008 | Abu El Ata et al. | |
| 7,533,038 B2 | 5/2009 | Blume et al. | |
| 7,561,158 B2 | 7/2009 | Abe et al. | |
| 7,565,304 B2 | 7/2009 | Casati et al. | |
| 8,019,582 B2 * | 9/2011 | Iliff | 703/11 |
| 8,666,926 B1 * | 3/2014 | Nease et al. | 706/50 |
| 8,682,704 B2 * | 3/2014 | Nease et al. | 705/7.19 |
| 2002/0002473 A1 | 1/2002 | Schrier et al. | |
| 2006/0085230 A1 | 4/2006 | Brill et al. | |
| 2006/0184391 A1 | 8/2006 | Barre et al. | |
| 2006/0265253 A1 * | 11/2006 | Rao et al. | 705/3 |
| 2008/0109252 A1 | 5/2008 | LaFountain et al. | |
| 2010/0205008 A1 | 8/2010 | Hua et al. | |
| 2010/0241459 A1 | 9/2010 | Rao | |

\* cited by examiner

*Primary Examiner* — Michael B Holmes
(74) *Attorney, Agent, or Firm* — Randy L. Canis, Esq.

(57) ABSTRACT

Methods and systems for improving therapy adherence are described. In an embodiment, a disease state associated with a member is identified. A member classification of the member is determined. The member classification may be based on past therapy the member received to treat a condition associated with the disease state. A diagnostic loop is selected based on the disease state associated with the member and the member classification. The diagnostic loop may include a plurality of operations. At least one of the plurality of operations of the diagnostic loop is performed. Other methods and systems are described.

27 Claims, 24 Drawing Sheets

1550

METHODS AND SYSTEMS FOR MEMBER MESSAGING

CROSS-REFERENCE TO RELATED APPLICATIONS

This application is a continuation-in-part of U.S. patent application Ser. No. 13/066,664, entitled "Methods and Systems for Improving Therapy Adherence," filed on Apr. 19, 2011, which claims priority to U.S. Provisional Patent Application No. 61/325,743, entitled "Methods for Improving Therapy Adherence," filed Apr. 19, 2010 and U.S. Provisional Patent Application No. 61/474,191 entitled "Methods for Improving Therapy Adherence," filed on Apr. 11, 2011, the entire contents of each of the applications are herein incorporated by reference in their entirety.

FIELD

This application relates generally to medical therapy adherence and, more particularly, to improving drug therapy adherence through methods of proactive outreach.

BACKGROUND

There is a continuing challenge to reduce the costs of health care. One of the biggest drivers of this cost is prescription drug coverage. Increased prescription drug adherence could lead to reduced waste in medical costs and productivity. Research has shown that non-adherence may have a profound effect on not only an individual's health, but on the health care system as a whole, costing up to $100 billion annually.

DETAILED DESCRIPTION

Figure 1:
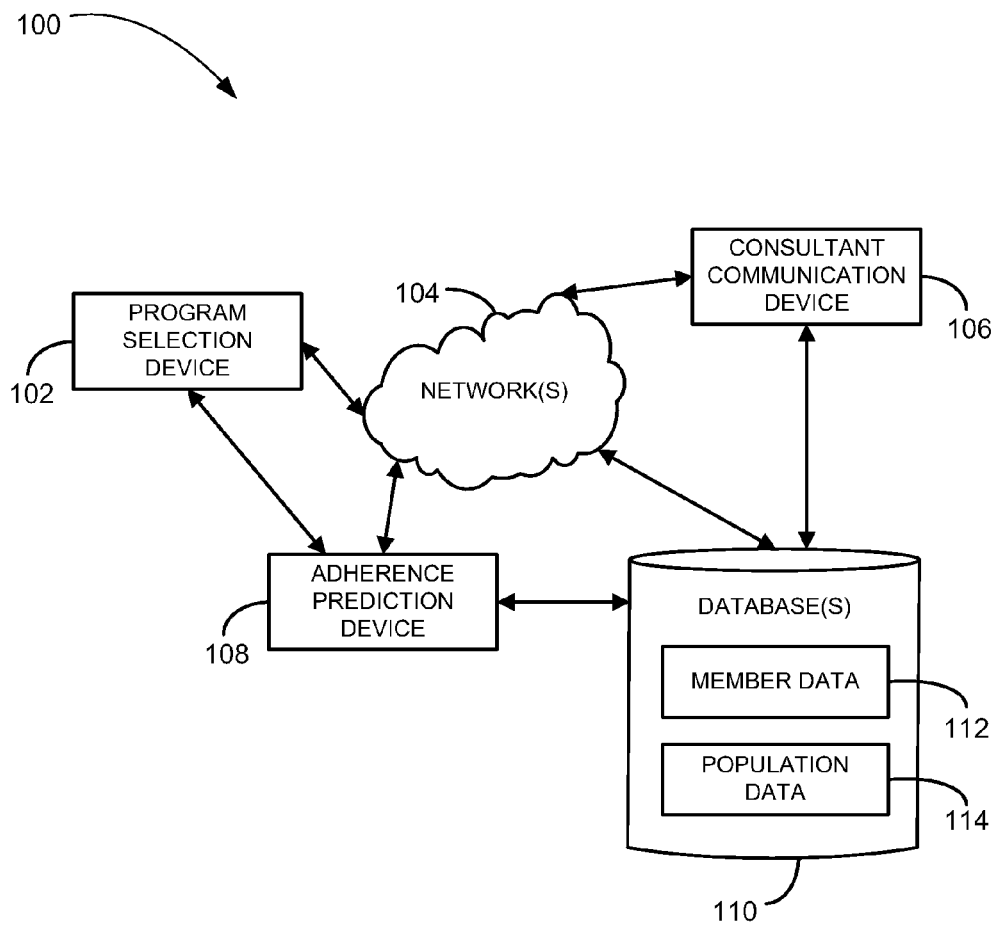
FIG. 1 is a block diagram of an example system, according to an example embodiment.

Example methods and systems for improving therapy adherence are described. In the following description, for purposes of explanation, numerous specific details are set forth in order to provide a thorough understanding of example embodiments. It will be evident, however, to one of ordinary skill in the art that embodiments of the invention may be practiced without these specific details.

The methods and systems are directed to improving adherence to therapy programs, in particular, to adherence to medication therapy and/or to healthcare therapy that includes medication therapy. The methods and systems may also be used to improve member compliance with and/or adherence to other wellness and/or health care programs.

Members may be employees of an employer group or otherwise associated with an employer group and receive some type of medical and/or pharmaceutical benefit through a health plan and/or a prescription drug plan associated with the employer group. An employer group may be a company, corporation, or similar entity that employs individuals but does not have the clinical abilities to provide healthcare for the individuals. Employees of an employer group may be referred to as members. People participating in a health plan may be referred to as members. Additionally, members may also be referred to as patients.

Generally, a client engages a pharmacy benefit manager (PBM) to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. The PBM may be a stand-alone PBM, or may be part of a larger organization that offers other benefits or services. The methods and systems may generally be used to guide a person who is a member of the drug benefit program offered by the client to pharmacies associated with a pharmacy network or pharmacy network association. Pharmacy networks and pharmacy network associations are interchangeably used herein.

The therapy adherence improvement tool may utilize predictive modeling coupled with historic data of a member (e.g., refill gap data) to prioritize member outreaches. Using a combination of demographic information, medical history of member, and other factors, a non-adherence index may be generated. Members identified as high-risk for non-adherence may receive an outreach or intervention sooner than members with a low risk of being non-adherent. In some embodiments, the outreach or intervention may consist of a diagnostic call to the member resulting from a tailored intervention based on the non-adherence index.

The methods and system described herein may eliminate unnecessary costs and reduce member disruption, as only members considered at high risk of not self correcting will receive an outreach. Tailored interventions may be offered, increasing the efficacy of the interventions. By predicting which members are at elevated risk in advance, adherence problems may be addressed proactively rather than reactively.

The methods and systems may include methods of identifying members who are at risk of non-adherence, non-compliance, or likelihood of cessation with a therapy program, predicting a basis for such noncompliance, and targeting interventions directed to members who have been identified as likely to be non-compliant, wherein interventions take into consideration the predicted basis for noncompliance and methods of proactive outreach to a member to intervene on a timely and consistent basis. In addition, the methods and systems may include methods of creating benefit plans that promote adherence to therapy programs comprising identifying members who are at risk of non-compliance with a therapy program, predicting a basis for such non-compliance, and structuring the benefit plan or program offering for such member to increase the likelihood of compliance and/or adherence and to reduce the likelihood of cessation of the therapy.

Factors and various demographics as well as historical compliance of the member may be used to predict whether a particular member is likely to be compliant with a therapy program; such factors may be included in a predictive tool, wherein the predictive tool may be used to predict the likelihood of therapy compliance.

The following are examples of compliance indicators that may be associated with therapy adherence: older age, greater income, higher disease severity, greater number of medications, symptomatic disease, being partnered, and partner adherence to maintenance medications.

Other factors that affect lack of adherence may include increasing cost (or copayment) of medications which may result in decrease of their use. However, the reverse may be true to a lesser extent: decreasing the cost/copayment for medications may have a very modest effect on increasing adherence.

The methods and systems may also include a method of improving therapy adherence such as promoting the home delivery channel (e.g., mail-order pharmacy). For example, members that are less likely to be adherent to a therapy program are identified and such members are targeted for promotion of home delivery of pharmaceuticals.

The methods and systems may be used to create benefit plans in which plans for those members identified as less likely to be compliant with therapy are structured to promote home delivery of pharmaceuticals. The methods and systems may determine the pharmaceutical delivery channel of a member. The pharmaceutical delivery channel may be a method by which the prescription drug is provided to a member (e.g., home delivery, mail order, retail fill, specialty fill, or otherwise). The methods and systems may also assess and detect a primary non-adherence cause for a member identified as likely to be non-compliant. Identifying member as likely to be non-compliant may occur simultaneously with identification of a primary non-adherence cause.

A member may be given a prescription drug as part of a therapy for a particular medical or health condition. In participating in drug therapy, the member taking the prescription drug may be considered adherent when the member takes the drug as prescribed. When the member does not take the prescription drug, or does not take the prescription drug as prescribed (e.g., the number of times per day and/or at the appropriate times per day), the member may generally be deemed to not be adherent. The methods and systems may be used to address failures in adherence to drug therapy and may be used to increase the likelihood that a member will adhere to his or her drug therapy.

Programs to increase adherence to drug therapy may include interventions. Examples of interventions may include letters or other communications to the member; use of home delivery and/or specialty pharmacy to fill and/or refill prescriptions; devices adapted to remind a member to take medication, notify a member if a dose has been missed, and/or remind a member that a refill is due; and/or changes to the cost for the drug therapy, e.g., a reduction in co-pay.

A therapy adherence proactive outreach (TAPO) method may also be implemented where the member is contacted by a therapy adherence consultant that contacts a member, by telephone, email, text messaging or other electronic communication method. The consultant may utilize a consultant user interface tool executing on a computing system. The consultant may be prompted with scripted questions to pose to the member in an attempt to correctly diagnose the reason(s) for non-adherence. The consultant may enter the member responses into a user interface and the consultant may be prompted with additional diagnostic questions to pose or may be prompted with helpful hints or alternative programs to offer the member that may assist in remedying the non-adherence. The scripted questions to be posed and the helpful hints and program offers may be part of a logic tree that is initiated by the computing system. One or multiple logic trees may reside on the computing system. If there are multiple logic trees, one may be selected over another as more appropriate for the given member based on demographics, predictive indicators, type of drug therapy, disease state and/or other factors. In another embodiment, there may be one large logic tree having major branches or pathways that may be selected based on the same type of factors. In either case, entire sections of the logic tree may be bypassed or shut off based on certain factors related to the member.

In an embodiment, a member may be contacted with a fully automated electronic computer-to-human communication system, a highly sophisticated Interactive Voice Response (IVR) systems, utilizing a sophisticated computer generated automated attendant voice and voice/speech recognition and/or touch tone recognition, Dual-Tone Multi-Frequency (DTMF) signaling technology to communicate with the member or the system may utilize other electronic communications such as text messaging, instant messaging, or web content. The intelligence of the system is provided by a logic tree of potential diagnostic questions that may be posed to the member. Therefore, rather than utilizing a live attendant or consultant with a consultant user interface that prompts the consultant/attendant, the system may be fully automated with a fully automated attendant where the intelligence of the automated attendants questions and the responses, hints or suggestions all stem from the logic tree.

In an embodiment, a potentially non-compliant member may be further identified as associated with one of three primary non-adherence causes. Sporadic forgetters are those member who have a positive perceived value of therapy and are not intentional in the adherence behavior. They may periodically neglect to take their medications, and as a result are not adherent.

Active decliners may not—for a variety of reasons—place a positive value on their therapy. This may be due to their belief that the medication is not effective, they may be experiencing side effects, they do not like being "prescribed for," or they do not believe the medication offers sufficient benefit relative to the cost. As a result, they actively choose not to take their medications as prescribed.

Refill procrastinators do a good job taking their medications as long as they have pills on hand. As their supply dwindles, however, they put off getting a refill. As a result, they may experience a gap in care. This behavior is less intentional than active decliners and does not reflect a negative view of therapy itself.

Having identified a member as at risk of non-adherence and/or having identified the primary non-adherence cause of a member, according to one embodiment, methods may further include targeting the identified members for intervention. The intervention may take into consideration the primary non-adherence cause of the member. Interventions may include, by way of example: letters combining authority (e.g., signed by chief medical officer and/or a physician) and loss aversion (pointing out risks of non-adherence rather than benefits of adherence); reduction of copayments; reminder systems (particularly effective for sporadic forgetters); auto-refill programs (particularly effective for refill procrastinators); financial assistance (particularly effective for active decliners); discussion with a clinician (particularly effective for active decliners).

The TAPO method may be utilized to diagnose the non-adherence problem independently or further diagnose the problem in addition to relying upon predictive methodology based on demographic, drug therapy type and disease state data. The TAPO method may also be utilized as a verification tool when non-adherence is predicted based on certain indicators. For example, if it is predicted that a given member will likely not adhere to a selected drug therapy, TAPO may be utilized to proactively contact the member to evaluate whether the prediction is the likely outcome. The predictive modeling techniques of the present disclosure may be uniquely applied to pharmaceutical data. For example, the methods and systems may be applied to data available to pharmacy benefit managers (PBMs). In one embodiment, a member identified as likely to be non-adherent may be provided with a container for his or her medication that incorporates reminding techniques. Products that are designed to provide member reminders may be targeted to the particular primary non-adherence cause of the identified member. Data gathered from such products may be used to predict the primary non-adherence cause of a member and identify other interventions that may be appropriate for the member, based on the predicted (or identified) primary non-adherence cause of a member.

An example of a method for improving adherence is the utilization of a product manufactured under the name GLOW-CAP by Vitality, Inc. and/or data available from use of such product. In one embodiment, a container (e.g., a prescription bottle capped with a GLOWCAP) may include a mechanism to determine whether it has been opened. In such instance, the medication may be presumed to have been taken. The GLOWCAP device for example, which may also include a wireless transmitter, may light-up when it is time for a dose of medicine. After a period of time (an hour, for example), the cap may emit a sound. The sound may vary, e.g., in tempo, complexity, and or volume as additional time passes. The particular change and/or timing of changes may be targeted based on the identified and/or predicted primary non-adherence cause of a member. Such a cap may be further programmed to send a message (e.g., email, text, phone call, and/or letter) to the member, a member advocate (e.g., a family member), and/or the physician of the member. The content and/or recipient of such message may be targeted based on primarily non-adherence cause of a member.

For example, a message to the physician of a member may be most effective for an active decliner whereas a text message to the member may be most effective for a sporadic forgetter. Other interventions to increase the adherence to therapy for a member may include type of pre-commitment, benchmarking of adherence against other member at an aggregated level, entrance into lotteries for member who take their medications each day, and other methods. By way of further example, members identified as at higher risk of non-adherence might escalate more quickly through the flashing, beeping and phone call reminders.

In one embodiment, members more likely to benefit from an intervention may be identified and/or targeted based on a health condition that is known (e.g., affirmatively included in member data available to a PBM or other party) or predicted (e.g., based on available data regarding prior prescriptions, treatments, and the like).

For example, members requiring therapy for depression, mental health issues, asthma, diabetes, hypertension, lipids, osteoporosis, multiple sclerosis, rheumatoid arthritis, and/or hepatitis C may particularly benefit from use of the methods and systems for improving therapy adherence. The applications of predictive modeling of the methods and systems may also be used to identify a window of time in which intervention is most likely to be effective. For example, a sporadic forgetter may benefit from periodic reminders whereas a refill procrastinator may benefit most from an intervention that occurs at or near the expiration of an existing prescription fill. Early interventions may be most effective for an active decliner.

In some embodiments, enrollment of members identified as likely to be non-adherent as identified via predictive modeling in specialty pharmacy program may lead to greater therapy adherence. By targeting specialty pharmacy programs for those members deemed more likely to be non-compliant and/or non-adherent based on behavioral characteristics of those members, the resources of the specialty pharmacy may be more effectively and efficiently used. Plan benefits may be designed to incorporate specialty pharmacy for such a targeted group of members.

Data used to predict the likelihood of therapy adherence by a member and/or a primary non-adherence cause of a member may include data points related to: demographics, e.g., age, gender, whether a partner is present, level of education, level of income (estimated or actual), place of residence, information about the prescribing physician, consumer behavior segmentation attributes such as NE66 segment, life stage grouping, prescription history, whether the member is a participant in concurrent therapy; past behavior, e.g., whether the member has been compliant on other medications, prior average compliance ratio for all "for life drugs"; other prescription data, e.g., the particular therapy class at issue, the co-pay of the member, whether the member participates in home delivery.

Thus, in one embodiment, predictive modeling techniques are applied to data points such as those listed above to: (1) rate the risk of non-adherence of a member; (2) prioritize outreach based on predicted risk and refill delay; (3) diagnose adherence problem (e.g., active decline; sporadic forgetter, or refill procrastinator); and (4) intervene as appropriate at member (patient) level.

The Predictive modeling techniques may include variable clustering. For example, the SAS procedure VARLCUS with centroid option may be used to cluster variables.

General claims data is unlikely to distinguish among the adherence problems (or categories of non-adherent members). The predictive modeling of the methods and systems may allow classifications not otherwise possible and may promote better and more targeted interventions.

Methods of the present disclosure may be used to identify members who are at risk of being non-adherent before they have a gap in a prescription refill and/or care. Medication Possession Ration (MPR) is a measure that captures a gap in therapy and may be used to measure adherence. MPR is able to detect a gap in care over a period of time. Often, late-to-fill measures are inaccurate because members may be keeping an extra supply on hand to ensure they don't run out and appear late to fill. MPR is a measure that may determine if a member has an adequate amount of medication on hand to adequately treat his or her condition. The MPR may be measured from the first fill of a prescription to the latest fill of the prescription, with the denominator being the duration from the index to the exhaustion of the last prescription and the numerator being the days supplied over that period from the first to last prescription. MPR may be calculated using the supply of medication to a member within a set measurement period divided by the number of days in the measurement period. According to one embodiment, outreaches are prioritized based on a combination of MPR and refill gap days. Members considered as highest risk of being non-adherent will receive an outreach much sooner (based on length of refill gap) than members with a low risk of being non-adherent. By way of example, an outreach may be a diagnostic call that results in a tailored intervention based on the reason for the refill gap.

Furthermore, methods and systems may eliminate unnecessary costs and member disruption as only members considered at high risk of not self correcting will receive an outreach. Second, tailored interventions may be offered, versus a one-size-fits-all solution. TAPO may be useful in providing a tailored approach by having various major branches of a logic tree or entire logic trees geared specifically for a particular non-adherence scenario. Finally, by predicting which members are at elevated risk in advance, methods and systems may promote proactive action, such as TAPO, rather than reactive action to therapy adherence problems.

Enrolling in a mail order pharmaceutical benefit program, e.g., a program in which prescriptions are fulfilled and medications are delivered to a member via mail or similar mechanism may provide significant benefits. Costs are typically lower, where "costs" may refer to the cost to the member, the cost to a health care plan sponsor (such as an employer, a managed care organization, a third party administrator, a purchasing coalition, or a labor union), and/or the cost to other parties involved in the distribution and/or payment chain. These types of programs may be initiated by a TAPO interaction with the member.

Additionally a mail order program may enhance member health by, for example, promoting and/or encouraging compliance with a treatment regimen. A method that promotes home delivery and that also provides for automated and/or default refills and/or renewal prescriptions may make it more likely that a member will obtain and administer a prescribed drug for the duration of the prescription period. Not only does such a method promote the health of the particular member, it may also promote public health, particularly if the member is suffering from a transmissible illness.

A prescription benefit plan will often offer a member a choice between filling a prescription (particularly a prescription for so-called "maintenance" medication and/or another medication in which a fill and/or refill is less time sensitive) at a retail pharmacy site or through a mail order pharmacy.

In some embodiments, the methods and systems may be used to promote home delivery in which a member is required to make an "active decision"—specifically, that requires a member to affirmatively select between retail fills (or refills) and home delivery fills. Even when no penalty is imposed for selecting retail fill over mail order fill for maintenance (or similar) medications (other than the consequence of not receiving the benefits of mail order), participation in mail order may be significantly increased.

In one embodiment, the following elements may be included: Pre-implementation; Rapid Response; and/or Retail Intervention Pre-implementation may include one or more communications with members and/or patients via, e.g., mail, telephone, email, facsimile, and/or other electronic and/or personal contact method to discuss home delivery and its benefits. Pre-implementation may also include communications about the "active decision" element. TAPO may be one of these pre-implementation communication methodologies.

"Pre-implementation" may refer to communications that, ideally, occur relatively early during the process of implementing a method of the invention. For example, pre-implementation may occur when a new prescription benefit plan is offered and/or at a period at or near renewal of a health plan. "Rapid response" is similar to pre-implementation and includes similar communications, but refers to communications triggered by circumstances that occur outside of the start-up phase of a new plan, a new enrollment period, and the like. For example, "rapid response" may be appropriate when a new employee is hired and/or begins to participate in a prescription benefit program. "Rapid response" may also be appropriate if a member begins taking a new medication, e.g., if a member makes a first fill of a prescription that may be a maintenance medication (based, e.g., on historical prescribing data for such medication).

As noted, a component may include an active decision element that in some manner promotes and/or requires an affirmative decision by a participant to select either retail or mail order. In one embodiment, the active decision is promoted and/or required as follows: (1) a set number of allowed retail fills is established, wherein "allowed retail fills" refers to retail fills (in particular, retail fills of maintenance or similar medications) that will be authorized under a prescription benefit plan before the required "active decision" has been made, and (2) when the set number of allowed retail fills has been reached, a retail fill will be initially denied in a "retail intervention." In an embodiment, retail intervention may include: (1) notice to the pharmacist or other employee at the retail site that communication with the PBM is required prior to fulfillment of the prescription; (2) communication between the member and the PBM is facilitated, preferably at the retail site, via a known communication technique, e.g., telephone; and (3) the member is informed that the number of allowed retail fills as been reached and is informed of the consequences for continued failure to make an active decision. The number of allowed retail fills may be between 2 and 5; for example 3. If the number of allowed retails fills is 3, then the $3^{rd}$ maintenance retail fill will trigger retail intervention.

In one embodiment, the consequence for failure to make an active decision after the number of allowed retail fills has been reached is that the member may be required to pay full price for the medication until an active decision has been made. If the retail intervention leads to an active decision, e.g., the member affirmatively selects either retail fill or mail order fill, the prescription fulfillment process continues either at the retail site or via the mail order program (depending upon the results of the active decision of the member) in accordance with the terms of the prescription benefit plan. For example, the agreed-upon co-payment is made by the member to receive the prescription.

The method may include communication to the members about the limit on retail fills absent an affirmative decision. For example, as part of re-implementation and/or rapid response, a member may be told of the number of allowed retail fills. In one embodiment, all retail fills (regardless of the type of medication) may be "counted" in determining whether the number of allowed retail fills has been reached. In an embodiment, only fills likely to be appropriate for mail order fulfillment (e.g., maintenance medications) are counted. In one embodiment, all retail fills are counted, but retail intervention will occur only with a retail fill likely to be appropriate for mail order. In an embodiment, all retail fills are counted and when the number of allowed retail fills has been reached, retail intervention will be implemented regardless of whether the particular prescription is appropriate for mail order. In such an embodiment, if a participant selects mail order, then if the particular prescription that prompted retail intervention is not appropriate for mail order, that prescription may be fulfilled at the retail pharmacy, but future prescriptions for mail order appropriate medications will be fulfilled by mail order. In some embodiments, such a prescription may be partially filled, e.g., with a number of units deemed likely to be sufficient until a mail order prescription will arrive at the designated mailing address.

In consideration of the richness of the input variable set, a method for dimension reduction may be utilized. Principal component analysis and other methods were considered. However variable clustering may be used as variable clustering may reduce the dimensionality of the model fit and scoring problem, thus simplifying the scoring method and each dimension selected by variable clustering may be used to represent a unique input variable from the original data set. This may ensure that the final scoring method has an intuitive description/explanation. The impact of each individual input may be ascertained directly without the need to interpret weighted combinations for principal components.

In some embodiments, variable clustering, using PROC VARCLUS, reduced input dimensions by approximately 40%.

The SAS procedure VARCLUS with centroid option may be used to cluster variables. Generally, this procedure collects into clusters variables that are highly correlated (parametrically and non-parametrically via Spearman's and Pearson's correlation coefficients) with each other yet oblique (but not filly orthogonal as in principal component) to other clusters. For each variable in each cluster a ratio (usually referred to as the R-square ratio) is computed as:

$$R \text{ square ratio} = (1 - R^2 \text{ own})/(1 - R^2 \text{ nearest})$$

Where $R^2$own is the fraction of the in-cluster variation explained by the variable, and $R^2$ nearest is the fraction of the nearest (not own) cluster variation explained by the variable. Selection may be made from each cluster of a representative that simultaneously represents its own cluster well (by explaining a large share of its own cluster variation) and is as orthogonal to other clusters as possible (by explaining only a small fraction of the variation of the nearest cluster). Such a candidate will have a small R square ratio.

Selection of a candidate may also be weighed in non-tangible factors such as: how intuitive is the candidate? How computationally expensive is it to compute? These factors may be used only as tie-breakers, and for the most part, the variable with the lowest R square ratio was selected as the cluster's representative. Due to the importance (and number) of therapy class variables, separate clustering exercises may be performed for concurrent therapy class and all other input variables.

To focus on the most promising input variables, bivariate screening may be performed on the remaining input variable set. The method may compute Spearman's rank correlation coefficient and Hoeffding's dependence coefficient (D-Statistic) for each remaining input variable against percent compliant. For each input variable, the method may plot the rank order of the Spearman correlation statistic vs. the rank order of the Hoeffding's D statistic. Variables at the upper-right corner of the plot may be eliminated from the input variable list. The rationale for this is that these variables have the least impact on percent compliant.

This plot may also be used to investigate non-monotonic associations. A high Spearman rank, together with a low Hoeffding's D rank, suggests that the relationship between input and percent compliant is not monotonic. These variables may be further explored using empirical logic plots.

Empirical logic plots may be recursively generated for each non-monotonic variable, and bins adjusted at each step, until the plots confirm that any non-linearity had been neutralized. A binned version of the variable may be created using the final bins. The binned variable may be given a b_prefix to differentiate it from its unbinned source. The benchmark model may be selected using PROC REG with SiEPWISE option. Questionable variables may be removed from the model specification, and predictive power and robustness may be reassessed. In cases where the impact of removal was marginal, the offending variables may be permanently removed.

In some embodiments, the method may handle adherence as not one behavior. The method may handle it as two sequential behaviors that are independent of one another. First, the member will either stay on their medication or not stay on their medication and conditioned on staying on their medication, they may either do a good job or they will do a bad job. The separation of behaviors allows the method to be more robust. The method may include a process where it goes through to look at the disease state and how long the member has been in a therapy program. A disease state may be the state of illness or other impediment or hindrance to the health of a person. Examples of a disease state may include, but are not limited to diabetes, hemophilia, multiple sclerosis, hypertension, asthma, and other health obstacles. Additional factors may be utilized when predicting the adherence probability of a member. The weighting that the method uses for those factors may be unique.

In some embodiments, the predictions that the method produces are created by multiplying the likelihood of continuing therapy times MPR. MPR may measure the amount of medication someone uses over a reporting period. For example, if there are 100 days in a reporting period and an individual is prescribed to take one pill a day and receives 100 pills, the ratio is calculated by 100 pills divided by 100 days, and the MPR indicates that the person is 100% adherent. If the person only obtained 50 pills in 100 days and the person is supposed to take one a day, they're 50% adherent. In some embodiments, MPR data may be collected by using drug claims.

If that reporting period starts on May 1, and someone got a prescription for 30 pills filled on April 25, the model may only provide credit for the part of the fill, the partial fill that started on May 1. The model may only count the number of pills that are actually in the reporting period in order to avoid the error of only counting the fills that actually occurred within the reporting period. However, taking an arbitrary window of time measurements for MPR may introduce noise. Therefore, the model may also evaluate the behavior of the member.

The model may determine when the person fills and measure the MPR based on the two points between which they got filled. For example, if the person received a fill on January 1st and the model detects a relatively large number of fills and the last fill detected for the year is November 30, then the model does not measure the number from January 1st to December 31$^{st}$, but only measures that number from January 1st to November 30th so that the measurement window is in accordance with the behavior of the member.

The method may utilize an adherence index rather than using a raw score. The adherence index may be determined from a model. The structure of the model may be determined by examining hundreds of variables for a given member or patient population and extrapolating behavioral patterns from the data. The model may examine data relating to member demographics or member data 112. Member data 112 may include, but is not limited to age, gender, profession, race, education, income, health insurance, residence, and marital status. Demographic information may be collected from the member, other healthcare vendors, claims data, or other source of information. Other data that may be examined include clinical data, claims data, prescription history, such as concurrent drug treatment and length of time on previous treatments, and past behavior such as cessation of other treatments and/or adherence on other medication treatments. Clinical data may include lab results, results of health screens, notations from a health care provider, medical imaging, medical history, and other information. A health screening may include, but is not limited to, the results of a physical, examination by physician, testing for a specific disease state, and other information. Claims data may include data associated with pharmacy claims (e.g., data related to prescriptions of a member, including cost, type, amount of medication, disease state, prescribing doctor) or medical claims (e.g., data related to claims submitted for medical costs and expenses incurred by the member for office visits or clinical testing). Probabilities may be determined using the identified behavioral patterns.

Once the basic models are obtained, real time data may be applied from current members to further refine the model. There is a probability variable in a cessation model that is indicative of the likelihood of a member to stop taking medication. The cessation model may be further divided or handled based on disease or therapy type. The cessation model may also be classified as a new patient and an experienced patient. A new patient may be a member who is new to a therapy whereas an experienced patient is a member who has already participated or continues to participate in the therapy.

The models may be used to target high risk members for outreach. The model may determine likelihood of cessation and if the probability of cessation is sufficiently low the model may determine what the likelihood of adherence is by developing an adherence index. Therefore, the model may have cessation model and an adherence model. Both models may be further divided into sub-models by a new patient model and an experienced patient model, thus resulting in four models.

In general, the adherence index may be determined by factoring the likelihood or probability of adherence developed from demographic data and other data patterns with the MPR of the member. Initially, the model may be built from general population historical demographic data and predicted MPRs. The general population data may also be further segregated by other factors such as by a particular community, or a population within a certain company or a population having a certain category of disease. Individual member demographics and other individual member data and individual member medication possession ratios may be applied against the model to further refine the model. The refinements may be made by evaluating differences between actual and predicted adherence and evaluating related patterns. Once actual data is gathered an actual past MPR of a member may be factored in to further refine the prediction model.

Probabilities regarding cessation and adherence may be developed by evaluating patterns from general historical demographic data and other data such as data for a given disease type or for a type of drug treatment. From these probabilities, a basic model may be developed. The basic model may be refined by correlating individual member demographics and actual member behavior with the basic model and updating the model as appropriate. For example, demographic data may include age, income bracket, severity of disease or disease type, number of concurrent medications, symptomatic disease, type of drug treatment, partner status, and partner adherence. The model may capture and statistically evaluate patterns in data that at first glance may appear unrelated to adherence and correlate the pattern to adherence. For example, the model may capture and statistically evaluate lifestyle patterns that have statistical significance to adherence. For example the model, may look at whether a member consistently gets their prescription refilled at the same location and correlate that to their likelihood of adherence. The model may also be enhanced by gathering member information by utilizing the TAPO method to extract member information from member responses to scripted questions posed. For example, a response of a member to prompts provided by TAPO may indicate a resistance to continuing a drug therapy because the member doubts the efficacy of the treatment or has problems with the type of treatment.

The adherence index may also identify the member as high risk, a likely barrier to adherence may also be determined such as forgetfulness, prescription refill delays or drug cost. From this information, the model may develop an individual member intervention program, which may include reminder tools, mail order subscriptions, and/or increased dosages requiring the medication be taken less often. The member intervention program may be decide based on what the model determines would be the most effective program for the given member, which may be based on historical modeling. Once an intervention program is implemented, the member may continue to be modeled and data may be collected and related to the adherence by the member and the adherence index may be continuously or periodically updated including the new information being gathered.

Improvements in the adherence index may be tracked and correlated in various ways. For example, the model may determine under what parameters a particular reminder device is most effective or in other words determining the "sweet spot" for a particular intervention program. This continued refinement of the sweet spot may improve the models ability to more efficiently target members who will be most likely to be impacted by intervention and determine a most effective intervention program for a given member.

In some embodiments, the use of the methods and systems may promote a more efficient allocation of resources by identifying members more likely to be responsive to an intervention. In some embodiments, the use of the methods and system may promote a more efficient allocation of resources by identifying members more likely to be responsive to a particular intervention. The method utilizes a probability predictive tool to target a member likely not to adhere.

In some embodiments, a member associated with a disease state may be identified using targeting. Running targeting may include loading and applying target data, such as a number of queries that may be defined (e.g., by a clinician). Targeting may then be used to identify members according to different attributes. Attributes may include, but are not limited to, disease states, geographic location, medication received, type of health insurance, or other type of information associated with members. Targeting may be run using the population data to identify one or more members. The targeting may be run weekly or with a different frequency to identify cases. Targeting may then be used to identify members according to different attributes. Attributes may include, but are not limited to, disease states, geographic location, medication received, type of health insurance, or other type of information associated with members. The targeting may not be immediately run to enable time for changes to the claims data due to error or other problems. In some embodiments, by running the targeting on the claims data that is recent, the patient evaluator can have access to timely information about the members. In some embodiments, providing more timely information to the patient evaluator provides a greater chance that the member will be receptive to or otherwise adopt the information and/or advice provided by the patient evaluator. Examples of results of targeting include identifying members who may need help with a first time medication, members who fill a prescription late, an abnormal behavior pattern for filing a prescription by members, or the like. Targeting may be run to identify members of a particular disease state.

An adherence index or probability of adherence may determine or calculated based on the targeting of the member and the disease state associated with the member. Based on the probability of adherence, an intervention for the member may be identified or determined.

In some embodiments, a diagnostic loop is selected based on the disease state of the member and the member classification. The diagnostic loop may include operations to obtain member data and transmit to the member data to improve adherence of the member to a prescription drug, an offer to improve adherence of the member to a prescription drug or both. The method may perform at least some of the operations of the diagnostic loop. The operations may include determining an intervention for the member based on a probability of adherence. The therapy adherence program may provide the intervention to the member. The intervention may include, but is not limited to a postal mail message, an electronic message, a text message, a transfer from automated messaging to a personal representative, a refill pill box, an auto-refill of a medication, and a late payment plan.

Determining the probability of adherence may include determining a probability of therapy cessation based on demographic data of the member and the disease state associated with the member; determining a probability of therapy compliance based on demographic data of the member and the disease state associated with the member; and calculating the probability of adherence of the member to the medication based on the probability of therapy cessation and the probability of therapy compliance.

The therapy adherence improvement program may also include arranging a health screening for the member based on the determination of the intervention.

FIG. 1 is a block diagram of an example system 100, according to an example embodiment. The system 100 is an example environment in which therapy adherence of members may be improved. The system 100 includes a program selection device 102 that may be in communication with a consultant communication device 106 over a network 104. The program prediction device 102 may be in communication with the consultant communication device when TAPO is utilized. TAPO may provide scripted questions to a member by way of a consultant user interface or a sophisticated IVR system and the member responses may be diagnosed by TAPO and certain hints are recommendations may be made to the member based on a logic tree and further diagnostics of the member responses may be requested from the program selection device.

The program selection device 102 may select a therapy program for a member that may increase the likelihood of the member adhering to a drug therapy. The program selection device 102 may select a diagnostic loop based upon the member disease state and member classification. Members may be categorized as new-to-therapy members or experienced-members. New-to-therapy members (also known as naïve members) are those members who do not have any experience with the prescription drug or drug therapy. Experienced members may include those members who have experience with the prescription drug or drug therapy. A diagnostic loop may include patient outreach logic which may include gathering demographic data associated with the member as well as providing information and offers to help the member improve or increase the likelihood of their adherence to the therapy.

Drug therapy adherence may refer to whether the member continues treatment or stops treatment of a drug for a particular condition. By way of example, if a member has a 30% likelihood of discontinuing therapy, he or she has a 70% likelihood of continuing therapy. Other scores (e.g., a scale from 0 to 1) may be used to identify a measured likelihood of continuing or discontinuing therapy.

The program selection device 102 may identify a therapy adherence program for a member, based on his or her likelihood of therapy adherence. In an example embodiment, a program selection may be a selection of no program or intervention if, e.g., no program has been identified as likely to increase therapy adherence or if the member is identified as so likely to be adherent that an intervention is unnecessary. The program selection device 102 may also be used to identify those members and corresponding programs that may be most likely to improve therapy adherence thus allowing resources to be targeted where they are relatively more likely to have a significant impact on therapy adherence. Therapy programs that may be more likely to be effective in improving therapy adherence of members with a particular likelihood of therapy adherence may be identified based on a score and/or range of scores.

The network 104 by which the devices 102, 106 communicate may include a Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

Communications with members before and/or after identified therapy programs have been implemented may be facilitated at the consultant communication device 106. For example, a patient consultant may use the consultant communication device 106 to facilitate communications with a member to gather data points for member data 112 stored in a database 110 that may be used to determine the likelihood of therapy adherence by a member. After a therapy program has been identified for a particular member, the consultant communication device 106 may be used to implement or aid in implementing the therapy program. For example, the consultant communication device 106 may generate communications to a member, may be used to offer home delivery to a member (and/or enroll a member in home delivery), and the like. One such communication method may be TAPO. Member may also have computing or personal digital assistant devices for receiving messages and other communications to improve adherence. Also special applications may be utilized on computing or personal digital assistant devices for management of medications and reminders.

Examples of patient consultants that may operate the consultant communication device 106 include a nurse, pharmacist, and other health care providers and/or personnel trained to administer and/or implement a therapy adherence program. The TAPO method may also be implemented where the member is contacted by a therapy adherence consultant that contacts a member, by telephone, email, text messaging or other electronic communication method. A consultant user interface of the tool may provide access to a consultant. The consultant may be prompted with scripted questions to pose to the member in an attempt to correctly diagnose the reason(s) for non-adherence. The consultant may enter the member responses into the user interface tool and the consultant may be prompted with additional diagnostic questions to pose or may be prompted with helpful hints or alternative programs to offer the member that may assist in remedying the non-adherence. The scripted questions to be posed and the helpful hints and program offers may be part of a logic tree that is initiated by the computing system. In another embodiment, a member may be contacted with a fully automated electronic computer-to-human communication system, a highly sophisticated Interactive Voice Response (IVR) systems, utilizing a sophisticated computer generated automated attendant voice and voice/speech recognition and/or touch tone recognition, Dual-Tone Multi-Frequency (DTMF) signaling technology to communicate with the member or the system may utilize other electronic communications such as text messaging, instant messaging, or web content. The intelligence of the system is provided by a logic tree of potential diagnostic questions that may be posed to the member. Therefore, rather than utilizing a live attendant or consultant with a consultant user interface that prompts the consultant/attendant, the system may be fully automated with a fully automated attendant where the intelligence of the automated attendants questions and the responses, hints, or suggestions all stem from the logic tree.

The adherence prediction device 108, in some embodiments, determines a predicted likelihood of continuing drug therapy by a member and predicted likelihood of complying with drug therapy. Compliance with drug therapy refers to how well a member complies with his or her therapy, assuming it continues. The MPR may be used to measure adherence or compliance of a member. If a member possesses a total of a 30 day supply of medication over a 45 day period, this indicates a failure to fully comply with the drug therapy. In one example embodiment, a lower MPR score indicates relatively poor compliance compared to a relatively high score indicating good compliance. Other compliance scores may be used. In an example embodiment, a modified MPR that measures MPR based on actual dates of fill is used. In an example embodiment, an MPR that measures MPR based on a predetermined or selected period of time is used. Predicted MPR may be used to measure, score, or otherwise identify a predicted likelihood of therapy compliance. In some example embodiments, the past MPR of a member when available may be used in connection with predicting the future MPR of a member.

Adherence, as identified via an adherence prediction device 108, is based on a combination of the likelihood of a member continuing therapy and a likelihood of a member complying with therapy. Adherence prediction as provided by adherence prediction device 108 may be a factor in determining whether or not to utilize the TAPO method and whether to select a logic tree for driving the TAPO interaction or to select a major branch or portion of a logic tree.

In one example embodiment, a separate subsystem is used based on whether a member is new to therapy (member is classified as a new-to-therapy member) or continuing therapy (member is classified as an experienced member). In another example embodiment, the same subsystem is provided for both naive and experienced members. The TAPO logic tree may vary also depending on whether the member is naive or experienced.

In one example embodiment, a separate subsystem is provided based on the disease state and/or drug therapy of the member. For example, one subsystem may be provided for a member with hypertension, another subsystem may be provided for a member with diabetes, and still another subsystem may be provided for a member with lipid disease. In one example embodiment, the subsystem is not dependent upon the disease state or drug therapy of the member. In an example embodiment in which separate subsystems are provided for both disease states and naive and experience members, then the adherence prediction device 108 may predict adherence for members with hypertension, diabetes, and lipid disease may include a naive hypertension subsystem, an experienced hypertension subsystem, a naive diabetes subsystem, an experienced diabetes subsystem, a naive lipid disease subsystem, and an experienced lipid disease subsystem.

Examples of the program selection device 102, the consultant communication device 106, and the adherence prediction device 108 include a gaming unit, a mobile phone, a personal digital assistant (PDA), a display device, a generic or specialized computing system, or the like. Other devices may also be used. The program selection device 102, the consultant communication device 106, and the adherence prediction device 108 may each use the same type of device, or may use different types of devices. Furthermore, while the system 100 in FIG. 1 is shown to include single devices 102, 106, 108, multiple devices may be used.

In some embodiments, the program selection device 102, the consultant communication device 106, and the adherence prediction device 108 are combined into a single server, while in other embodiments, the program selection device 102, the consultant communication device 106, and the adherence prediction device 108 operate on separate servers.

The program selection device 102, the consultant communication device 106, and the adherence prediction device 108 may be in communication with a database 110. The database 110 may store member data 112 and population data 114. The member data 112 may include member data received by the consultant communication device 106. One source of the member data 112 may be derived using the TAPO method where the member data 112 is extracted from the member responses received during the TAPO and the extracted data may be included with the member data 112 to be stored in the database. The member data 112 may include member demographics data, member prescription history data, past prescription behavior data of the member and/or TAPO member responses data. The member data 112 may be obtained by a patient consultant, during a TAPO session for example, from prescription claim histories, health plan information, and the like. The member past prescription data may include information that identifies the member, as to a particular drug therapy, as new (naive) or experienced.

The population data 114 may include population demographics data, population prescription history data, and/or population past prescription behavior data. The population may include a set of individuals who have participated in and/or who have been prescribed one or more drug therapies and/or who are identified as having a particular disease or condition. Other populations may be used such as populations in communities or populations at certain companies of populations meeting certain demographic criteria. Population demographics data generally includes information about one or more demographic characteristics of a population such as age, gender, income or income range, race, place of residence, employment, and other demographic characteristics. Population prescription history data generally includes information about one or more prescription history characteristics, such as information about concurrent therapies. Population past prescription behavior data generally includes information about one or more past prescription behavior characteristics, such as selection of brand or generic drugs, use of retail or home delivery, adherence to other drug therapies, and the like.

The member data 112 may be similar to the population data 114 but includes information about the characteristics that is specific to the member for whom a therapy adherence program may be identified and/or implemented.

Figure 2:
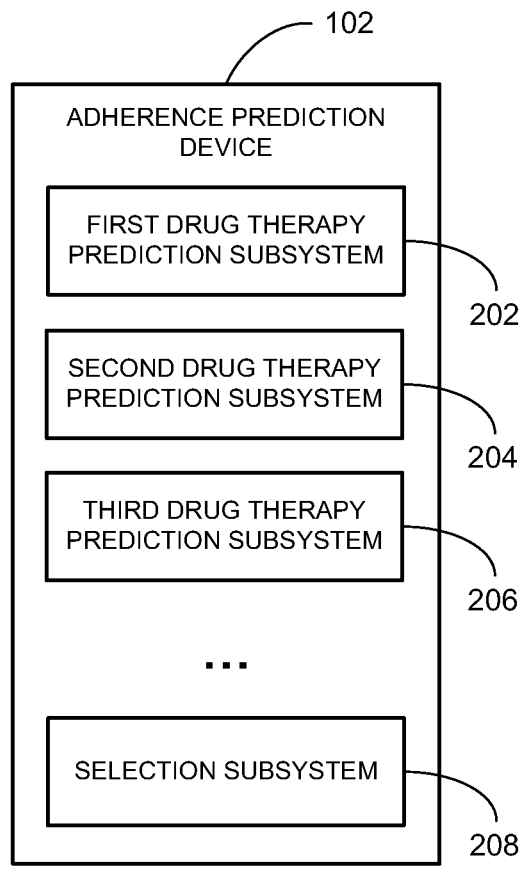
FIG. 2 illustrates an example adherence prediction device that may be deployed in the system of FIG. 1, according to an example embodiment.

FIG. 2 illustrates the adherence prediction device 108, according to an example embodiment. The adherence prediction device 108 includes one or more subsystems employed to predict adherence for each of a set of conditions and/or drug therapy. The adherence prediction device 108 with the subsystems may be deployed in the system 100, or may be deployed in another system.

The adherence prediction device 108 as shown in FIG. 2 includes a first drug therapy prediction subsystem 202, a second drug therapy prediction subsystem 204, a third drug therapy prediction subsystem 206, and a selection subsystem. More or less subsystems may be used.

By way of example, the first drug therapy prediction subsystem 202 may be used to predict adherence for hypertension members, the second drug therapy prediction subsystem 204 may be used to predict adherence for diabetes members, and the third drug therapy prediction subsystem 206 may be used to predict adherence for members with lipid disease. In another example embodiment, a separate prediction subsystem is deployed for members who are new to a particular drug therapy and for those who are experienced with the drug therapy. The selection subsystem 208 may be used to identify the particular drug therapy prediction subsystem to be deployed in predicting a likelihood of compliance for a member.

Figure 3:
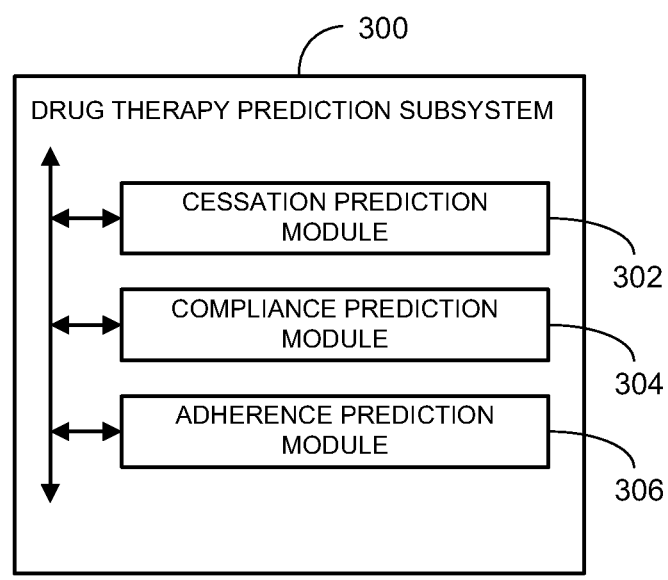
FIG. 3 illustrates an example drug therapy prediction subsystem that may be deployed in the adherence prediction device of FIG. 2, according to an example embodiment.

FIG. 3 illustrates a drug therapy prediction subsystem 300, according to an example embodiment. The drug therapy prediction subsystem 300 may be deployed as a drug prediction subsystem of the prediction subsystems 202-206 in the adherence prediction device 108 of the system 100, or may otherwise be deployed in another system.

The drug therapy prediction subsystem 300 may include a cessation prediction module 302, a compliance prediction module 304, and/or an adherence prediction module 306. Other modules may also be included. In some embodiments, the modules of the drug therapy prediction subsystem 300 may be distributed so that some of the modules are deployed in the adherence prediction device 108 and some modules are deployed in the program selection device 102 and/or the consultant communication device 106. In one embodiment, the modules are deployed in memory and executed by a processor coupled to the memory.

The cessation prediction module 302 predicts the likelihood that a member discontinues a particular drug therapy. The compliance prediction subsystem 304 predicts the likelihood that a member complies with a particular drug therapy. The adherence prediction subsystem 306 predicts the likelihood of the adherence of the member.

The drug therapy prediction subsystem 300 may also include other modules. Examples of other modules include a disease state identification module, a member classification module, a therapy selection module, and a therapy outreach module. The disease state identification module may identify a disease state associated with a member. A member classification module may determine member classification of the member. The member classification may be based on past therapy the member received to treat a condition associated with the disease state. A therapy selection module may select a diagnostic loop based on the disease state associated with the member and the member classification. The diagnostic loop may include multiple operations. The multiple operations may include obtaining member data 112 and transmitting, to a member, information to improve adherence of the member to a prescription drug, an offer to improve adherence of the member to a prescription drug, or both. An offer may be in the form of a text message, email, instant message, letter, telephone call or other means of communication with the member.

The methods and systems may also include identifying a prescription drug associated with the member (the prescription drug prescribed to treat a condition associated with the disease state), determining the member is taking the prescription drug as prescribed, determining a pharmaceutical delivery channel associated with the medication. The operations may include identifying a prescription drug associated with the member, determining the member is not taking the prescription drug as prescribed, determining that the member is taking some of the prescription drug to treat the condition associated with the disease state, requesting information to determine why the member is not taking the medication as prescribed.

The operations may include transmitting a home delivery switch offer responsive to receiving the response. The response may indicate that the member forgot to renew the prescription drug, the member cannot afford the prescription drug, or the member forgot to refill the prescription drug.

The system may transfer the member to a care coordinator responsive to receiving the response if the response indicates that the member has a question regarding the prescription drug or the member forgot to take the prescription drug.

The operations may include transmitting a pillbox offer if the member indicates that they forgot to take a dose of the prescription drug. If the system receives a rejection for the pillbox offer, then a home delivery switch offer may be transmitted to the member.

The operations may include accessing pharmacy claims data associated with the member; determining the member is refilling a different medication at a retail pharmacy based on the pharmacy claims data associated with the member; and transmitting a home delivery switch offer responsive to the determination.

The operations may include accessing clinical data associated with the member; and determining the member has received the past therapy to treat the condition associated with the disease state. The medication may be prescription medication or over-the-counter (OTC) medication. A therapy outreach module may perform some of the operations of the diagnostic loop.

The pharmaceutical delivery channel may be retail or mail order/home delivery. The offer to improve adherence of the member to the prescription drug may include a home delivery switch offer. A home delivery switch offer is an offer that would enable the member to switch from retail pharmaceutical delivery channel to a mail order or home delivery pharmaceutical delivery channel. The offer may include connecting the member via phone, instant messenger or other communication channel to a care coordinator to transition the prescription drug or any medication prescribed to the member from retail filling to home delivery filling. If the pharmaceutical delivery channel is already the mail order pharmacy, the offer to improve adherence may include an offer to include an automatic refill for the prescribed drug where the automatic refill for the prescribed drug is fulfilled by the mail order pharmacy.

If the member chooses to accept any of the above offers, the system may connect the member to a care coordinator who will enable or facilitate the completion of the offer. The system may also record the acceptance or rejection of any offer by the member.

Figure 4:
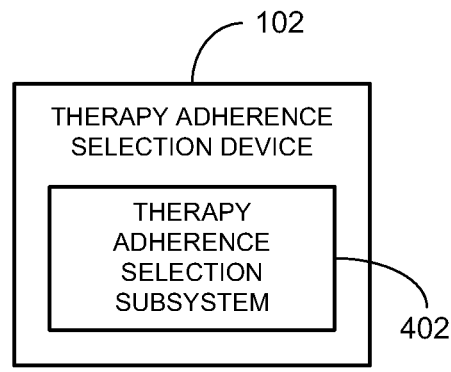
FIG. 4 illustrates an example program selection device that may be deployed in the system of FIG. 1, according to an example embodiment.

FIG. 4 illustrates the program selection device 102, according to an example embodiment. The program selection device 102 includes a program selection subsystem 402. The program selection subsystem 402 identifies a therapy program likely to increase a therapy adherence of a member based on the predicted therapy adherence of the member. For example, communications (e.g., letters or e-mails) have been identified as likely to increase adherence of a member who is moderately likely to adhere to therapy and devices (e.g., GLOW-CAP devices or DOSE-ALERT devices) have been identified as likely to increase adherence of a member who is less likely to be adherent. Utilization of the TAPO method may be one type communication with a member. The therapy adherence selection device and the therapy adherence selection subsystem may communicate with the consultant communication device to provide predicted therapy adherence information to be utilized by the TAPO method for logic tree selection and/or logic tree navigation. Accordingly, if a likelihood of adherence of a member falls within the range for which communications have been identified as a likely successful program, a communication program is identified for that member by the program selection subsystem 402. The program selection device 102 with the program selection subsystem 402 may be deployed in the system 100, or may be deployed in another system.

Figure 5:
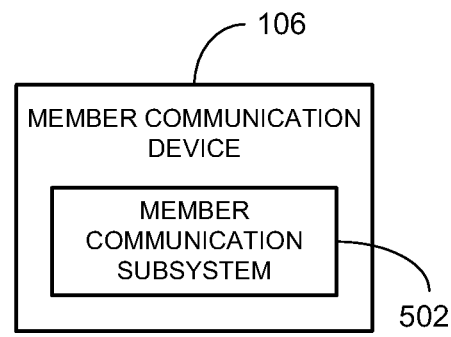
FIG. 5 illustrates an example consultant communication device that may be deployed in the system of FIG. 1, according to an example embodiment.

FIG. 5 illustrates the consultant communication device 106, according to an example embodiment. The consultant communication device 106 may be communicable with a member communication device and may include a member communication subsystem 502. The consultant communication device 106 may be communicable with a member communication device and with the member communication subsystem 502 may be deployed in the system 100, or may be deployed in another system. The member communication device and the member communication subsystem may be utilized with TAPO to provide TAPO diagnostic communications with the member.

Figure 6:
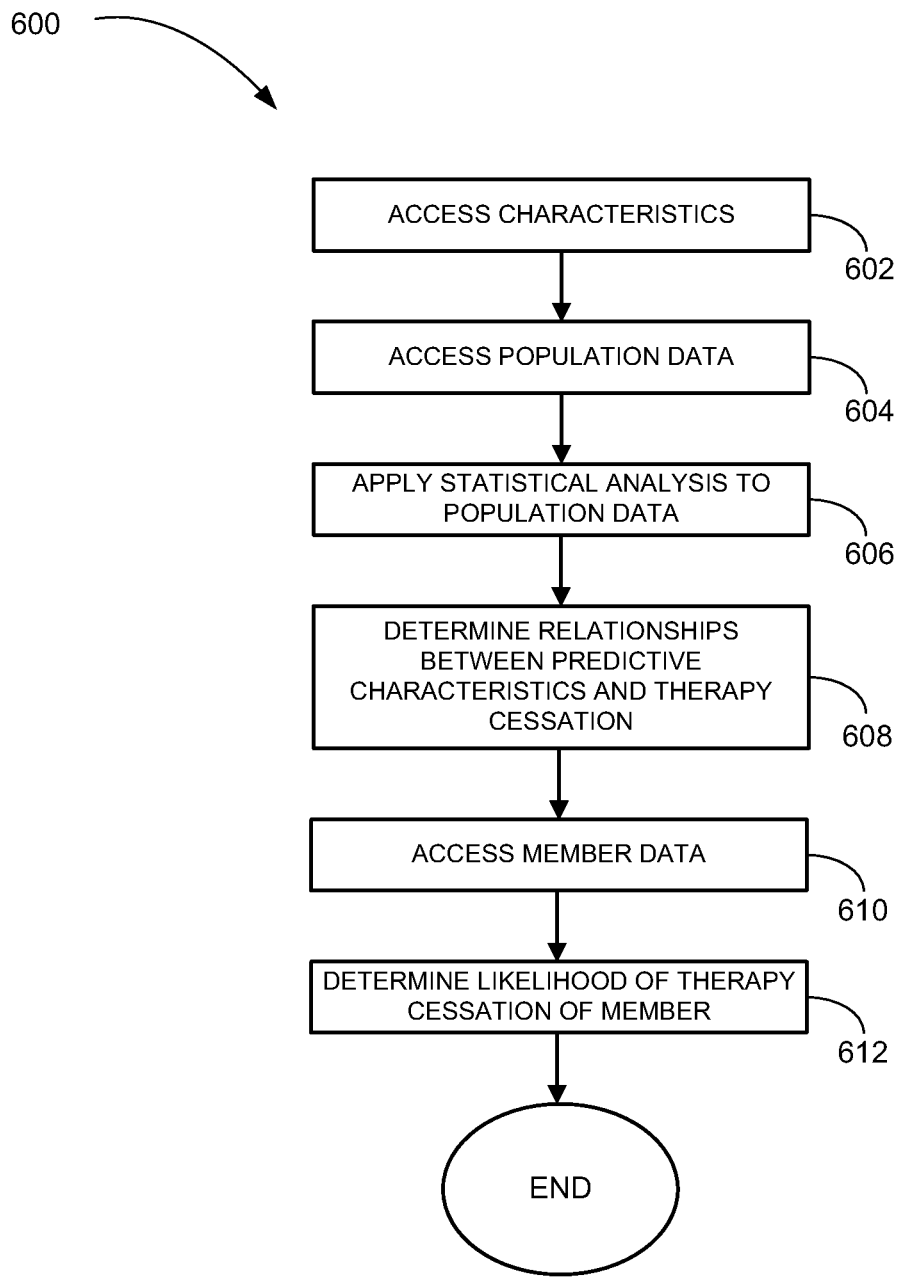
FIG. 6 is a block diagram of a flowchart illustrating a method of predicting likelihood of cessation of therapy, according to an example embodiment.

FIG. 6 illustrates a method 600 of predicting likelihood of cessation of therapy, according to an example embodiment. The method 600 may be performed by the adherence prediction device 108, or may be otherwise performed. In some embodiments, the method 600 may be performed by the cessation prediction module 302 (see FIG. 3).

At block 602, a set of characteristics that may be predictive of therapy cessation is accessed. Population data is accessed at block 604. At block 606, statistical analysis techniques are applied to the population data to identify predictive characteristics. In some embodiments, the identified characteristics are characteristics that are predictive of therapy cessation. At block 608, a determination is made of the relationships between the predictive characteristics and therapy cessation. In some embodiments, the resulting determination is a co-variance. In some embodiments, statistical regression analysis techniques may be used to determine the relationships.

The operations performed at blocks 602-608 need not be carried out in each instance in which a therapy adherence program is identified for a particular member or in which the likelihood of therapy cessation is determined. In an example embodiment, the results of the operations, once performed, are retained for future use. In an example embodiment, the operations are periodically repeated to identify new predictive characteristics and/or new relationships. At block 610, the member data 112 for each predictive characteristic is accessed. As discussed above, member data extracted from member responses made during a TAPO session may be stored as part of this data. At block 612, the likelihood of therapy cessation of a member is determined based on the relationships between the predictive characteristics and likelihood of therapy cessation.

Figure 7:
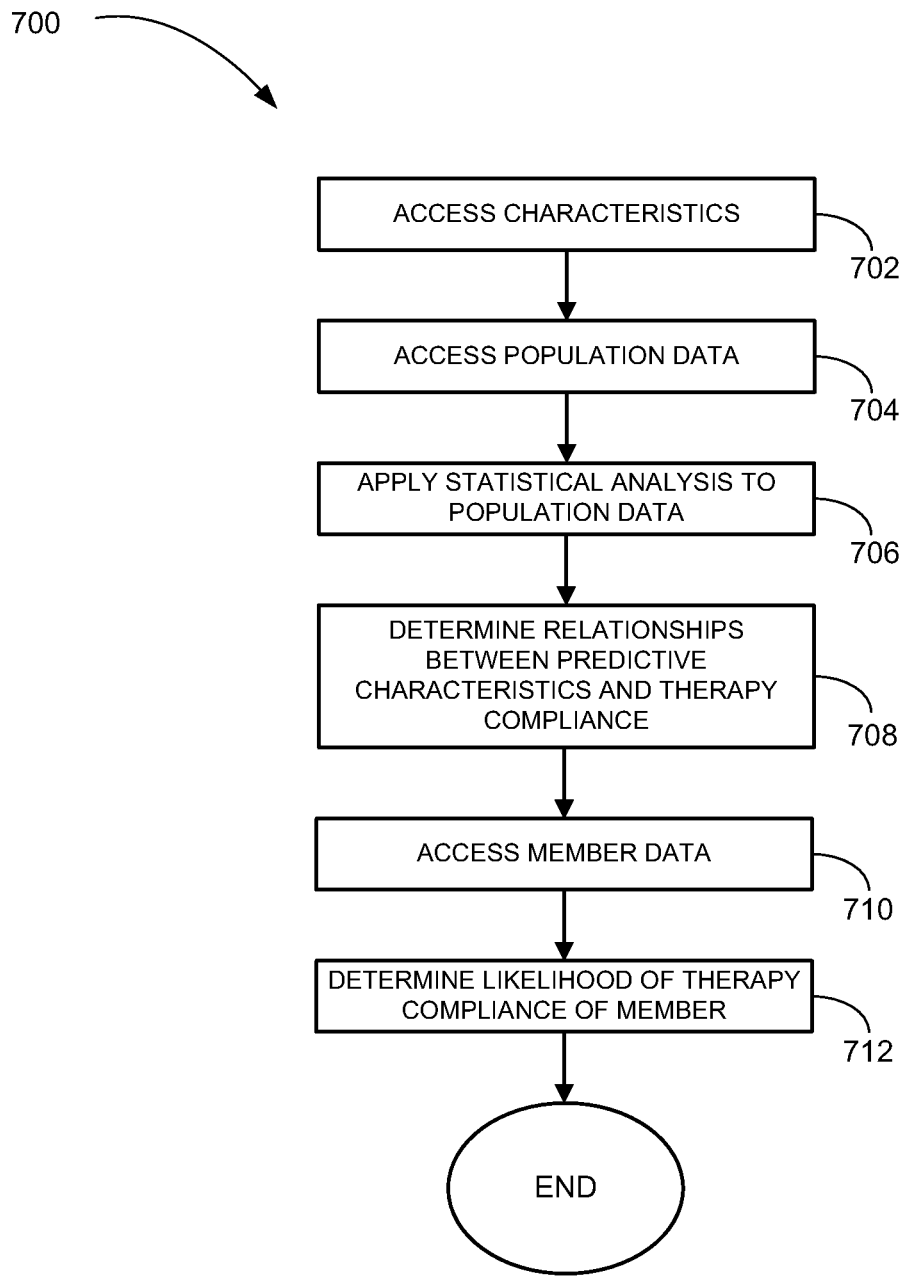
FIG. 7 is a block diagram of a flowchart illustrating a method of predicting therapy compliance, according to an example embodiment.

FIG. 7 illustrates a method 700 for predicting therapy compliance, according to an example embodiment. The method 700 may be performed by the adherence prediction device 108, or may be otherwise performed. In some embodiments, the method 700 may be performed by the compliance prediction module 304 (see FIG. 3). At block 702, a set of characteristics that may be predictive of therapy compliance is accessed. Population data is accessed at block 704.

At block 706, statistical analysis techniques are applied to the population data to identify predictive characteristics. In some embodiments, the identified characteristics are characteristics that are predictive of therapy compliance. At block 708, a determination is made of the relationships between the predictive characteristics and therapy compliance. In some embodiments, the resulting determination is a co-variance. In some embodiments, statistical regression analysis techniques may be used to determine the relationships.

The operations performed at blocks 702-708 need not be carried out in each instance in which a therapy adherence program is identified for a particular member or in which the likelihood of therapy compliance is determined. In an example embodiment, the results of the operations, once performed, are retained for future use. In an example embodiment, the operations are periodically repeated to identify new predictive characteristics and/or new relationships. At block 710, the member data 112 for each predictive characteristic is obtained. At block 712, the likelihood of therapy compliance by a member is determined based on the relationships between the predictive characteristics and likelihood of therapy compliance.

Figure 8:
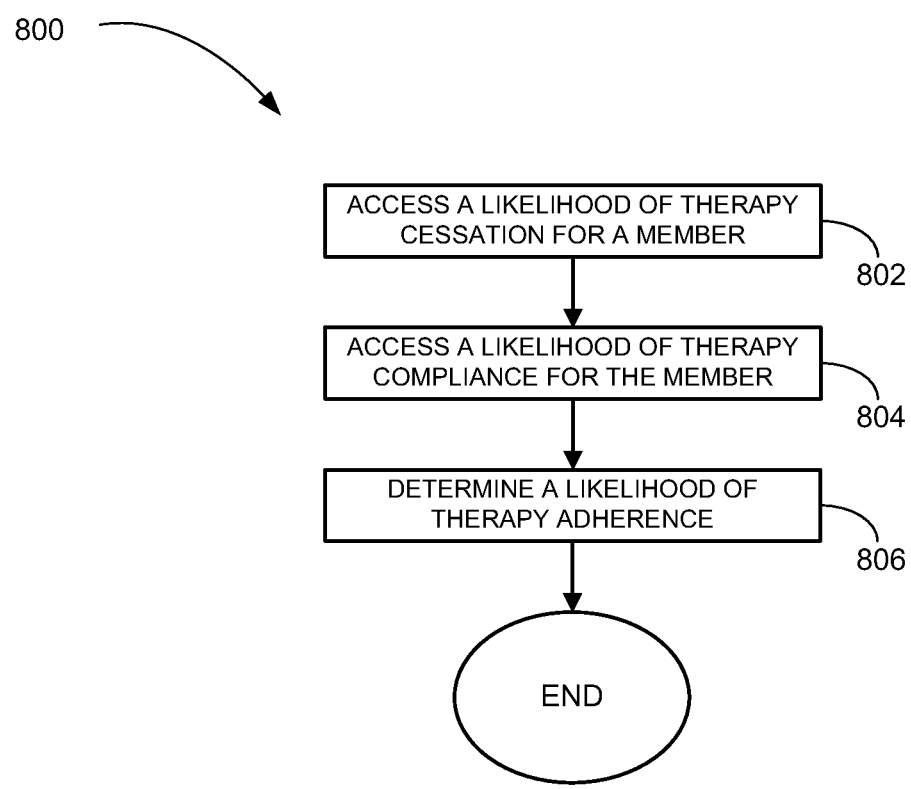
FIG. 8 is a block diagram of a flowchart illustrating a method of predicting therapy adherence, according to an example embodiment.

FIG. 8 illustrates a method 800 for predicting therapy adherence, according to an example embodiment. The method 800 may be performed by the adherence prediction device 108, or may be otherwise performed. In some embodiments, the method 800 may be performed by the adherence prediction module 306 (see FIG. 3). A likelihood of therapy cessation of a member is accessed at block 802. The likelihood of therapy compliance by a member is accessed at block 804.

The likelihood (or probability) of therapy adherence of a member is determined at block 806 based on the likelihood of therapy cessation and therapy compliance of the member. For example, the likelihood of therapy cessation and therapy compliance of the member may be multiplied, added, or otherwise combined. The likelihood of therapy cessation and/or therapy compliance of the member may be weighted in the calculation. Because you can only continue or stop a therapy, the sum of the predictions will equal 1. (e.g., predicted cessation+predicted persistence=1).

Figure 9:
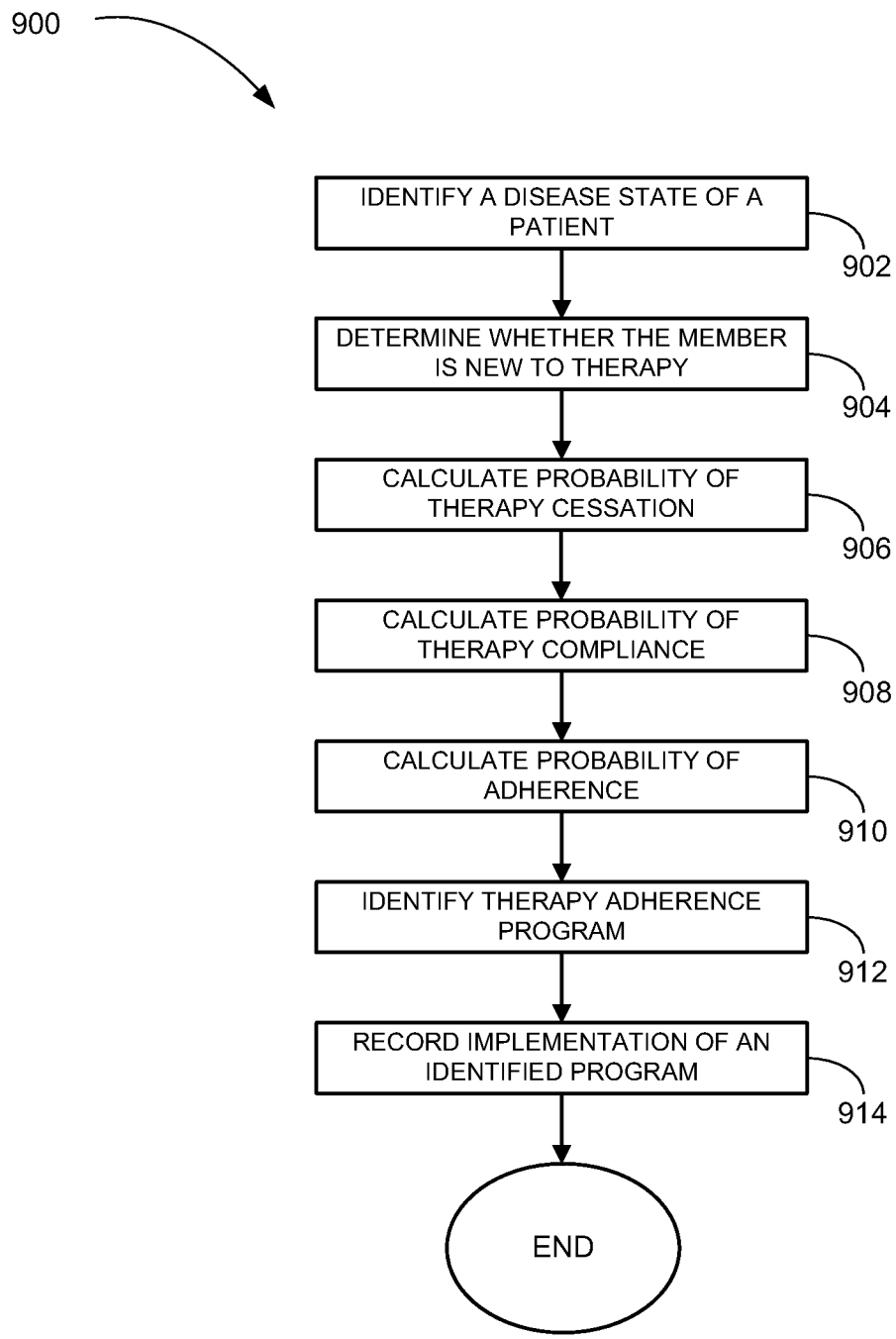
FIG. 9 is a block diagram of a flowchart illustrating a methods for therapy program implementation, according to an example embodiment.

FIG. 9 illustrates a method 900 for therapy program implementation, according to an example embodiment. The method 900 may be used to improve the likelihood of therapy adherence of a member. The method 900 may be performed by the adherence prediction device 108, partially by the adherence prediction device 108 and partially by the program selection device 102 and/or the consultant communication device 106, or may be otherwise performed.

A disease state of a member is identified at block 902. A disease state of the member may be identified based on the member data 112, through the consultant communication device 106, or may be otherwise identified. Examples of the disease state of the member may include hypertension, diabetes, and lipid disease, asthma, hyperlipidemia, multiple sclerosis, and hemophilia.

Other disease states may also be used. The probability of therapy cessation is calculated at block 906. The probability of therapy compliance is calculated at block 908. The probability of adherence of the member is calculated at block 910. A therapy adherence program (e.g., an intervention) is identified at block 910 based on the probability of adherence of the member.

An implementation of an identified program may be recorded at block 912. The therapy adherence program may be implemented through the consultant communication device 106, or may be otherwise implemented.

Figure 10:
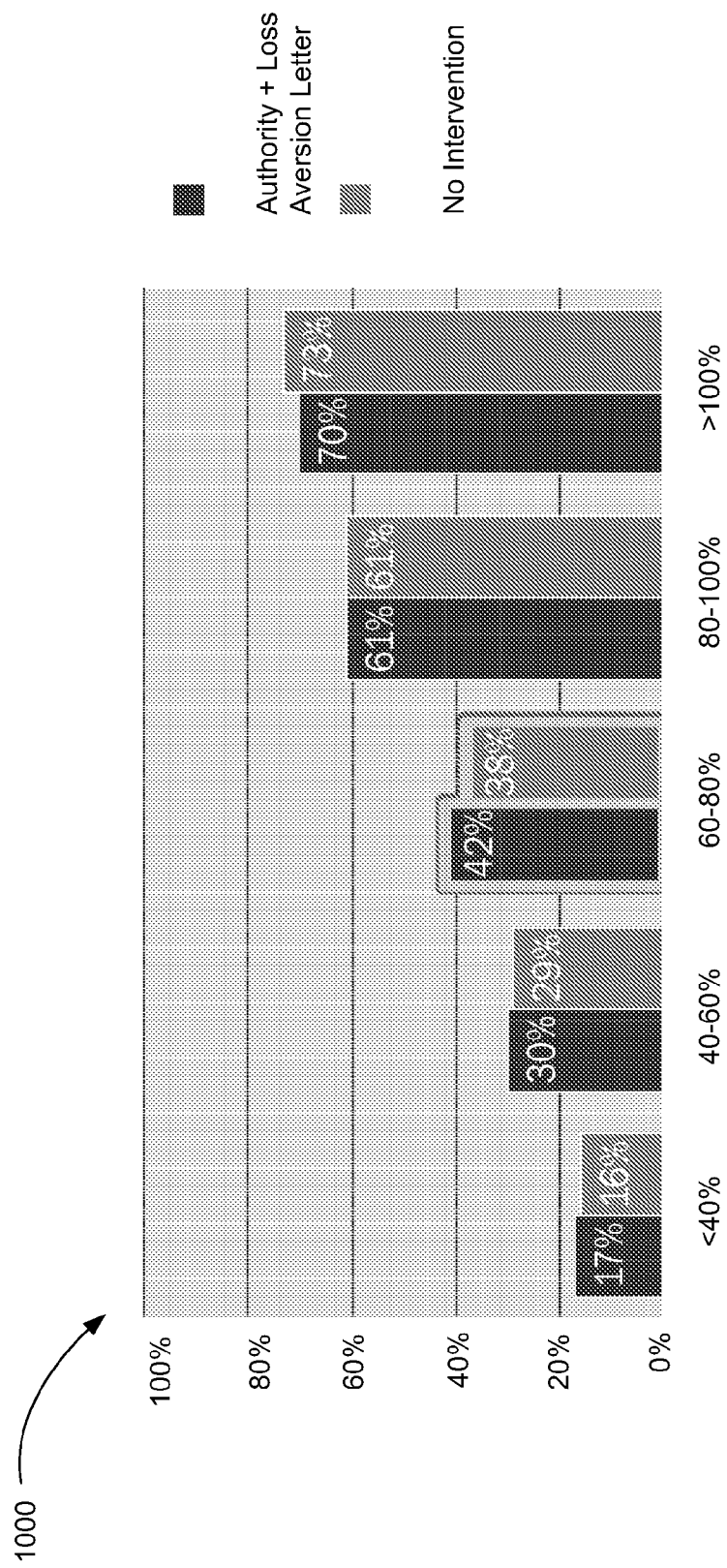
FIGS. 10 and 11 are charts, according to example embodiments.

FIG. 10 is an example chart 1000, according to an example embodiment. The chart 1000 indicates an example study of a population. A certain portion of the population having a low adherence rate may be targeted.

Figure 11:
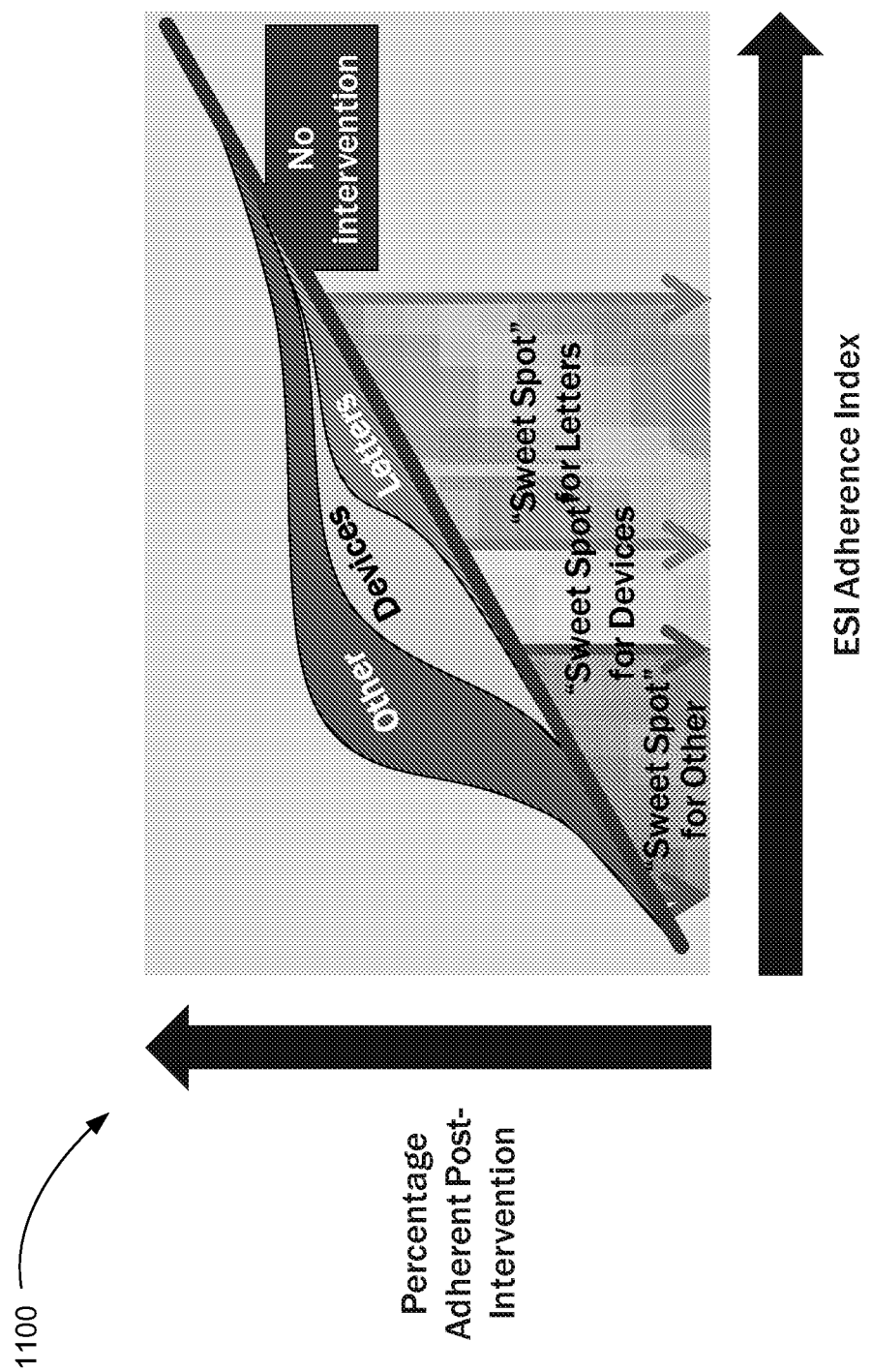

FIG. 11 is an example chart 1100, according to an example embodiment. The chart 1100 indicates the percentage adherent post intervention. The chart 1100 reflects a "sweet spot" were a particular type of intervention may have a higher degree of effectiveness than other segments of the population.

Figure 12:
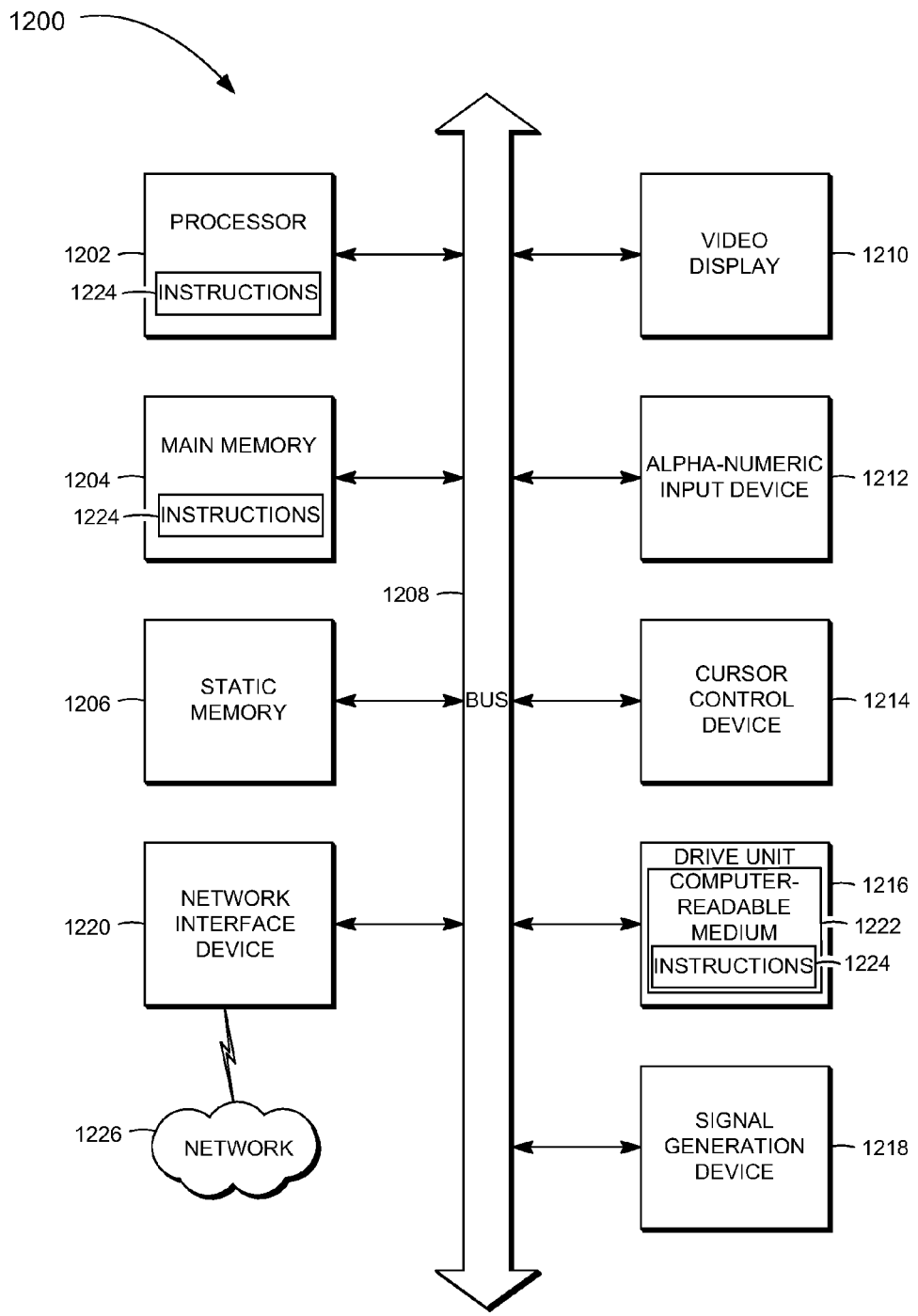
FIG. 12 is a block diagram of a machine in the example form of a computer system within which a set of instructions for causing the machine to perform any one or more of the methodologies discussed herein may be executed.

FIG. 12 shows a block diagram of a machine in the example form of a computer system 1200 within which a set of instructions may be executed causing the machine to perform any one or more of the methods, processes, operations, or methodologies discussed herein. The program selection device 102, the consultant communication device 106 including the member communication device, and/or the adherence prediction device 108 may include the functionality of the one or more computer systems 1200. For example, in a TAPO method a consultant and a member may be communicably linked over a wide area network where the consultant may have a computing system that provides a user interface to provide access to a consultant, driven by the TAPO method, of underlying logic tree for posing questions to the member and for inputting responses from the member. The member may also have a computing system with a member user interface where the member may receive questions posed and provide responses.

In an example embodiment, the machine operates as a standalone device or may be connected (e.g., networked) to other machines in a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Further, while only a single machine is illustrated, the term "machine" shall also be taken to include any collection of machines that individually or jointly execute a set (or multiple sets) of instructions to perform any one or more of the methodologies discussed herein.

The example computer system 1200 includes a processor 1212 (e.g., a central processing unit (CPU) a graphics processing unit (GPU) or both), a main memory 1204 and a static memory 1206, which communicate with each other via a bus 1208. The computer system 1200 may further include a video display unit 1120 (e.g., a liquid crystal display (LCD) or a cathode ray tube (CRT)). The computer system 1200 also includes an alphanumeric input device 1212 (e.g., a keyboard), a cursor control device 1214 (e.g., a mouse), a drive unit 1216, a signal generation device 1218 (e.g., a speaker) and a network interface device 1220.

The drive unit 1216 includes a computer-readable medium 1222 on which is stored one or more sets of instructions (e.g., software 1224) embodying any one or more of the methodologies or functions described herein. The software 1224 may also reside, completely or at least partially, within the main memory 1204 and/or within the processor 1212 during execution thereof by the computer system 1200, the main memory 1204 and the processor 1212 also constituting computer-readable media.

The software 1224 may further be transmitted or received over a network 1226 via the network interface device 1220. While the computer-readable medium 1222 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer readable medium" shall accordingly be taken to include, but not be limited to, solid-state memories, and optical media, and magnetic media.

Figure 13A:
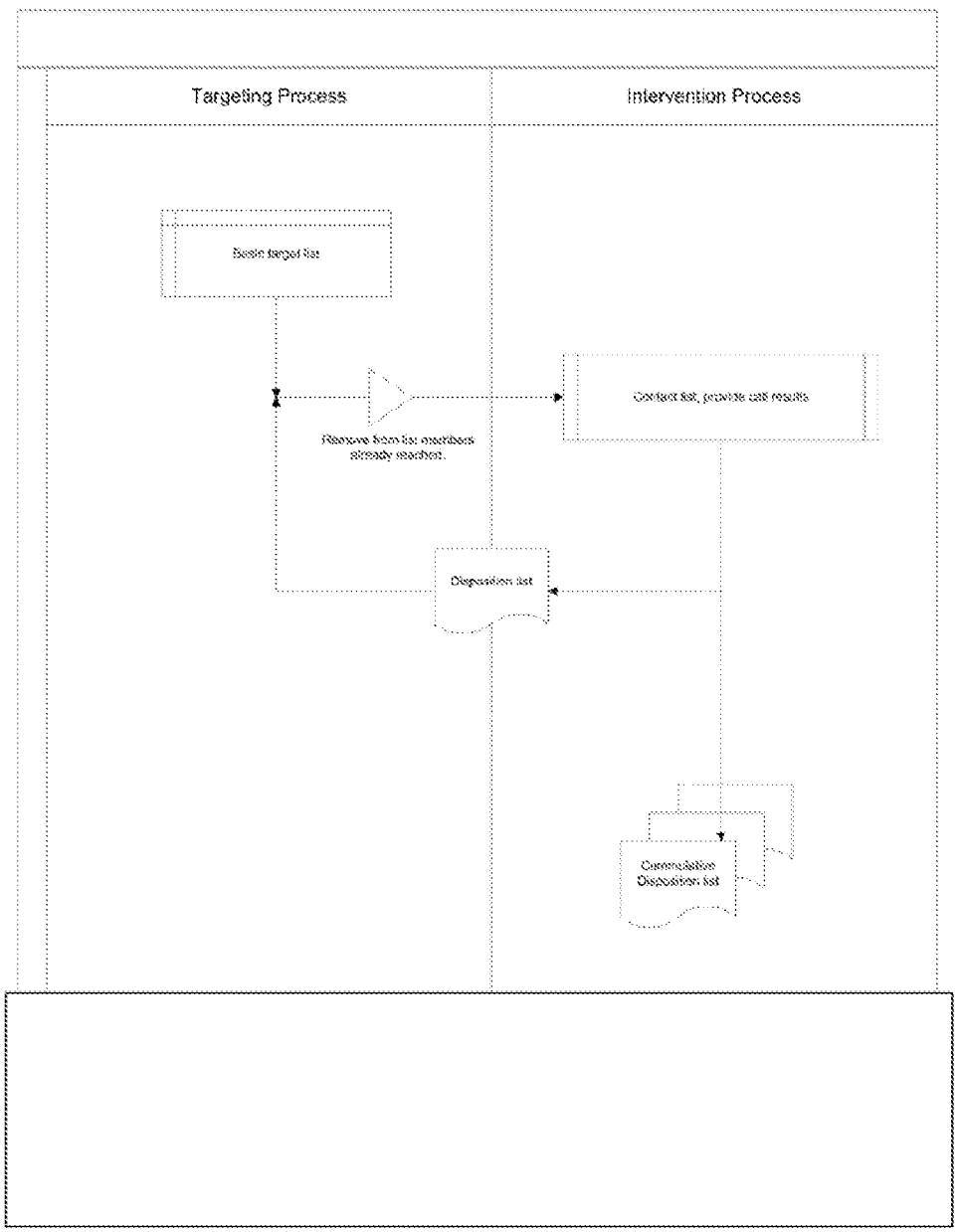
FIGS. 13A, 13B and 13C are a block diagram of the top level process flow, according to an example embodiment.
Figure 13B:
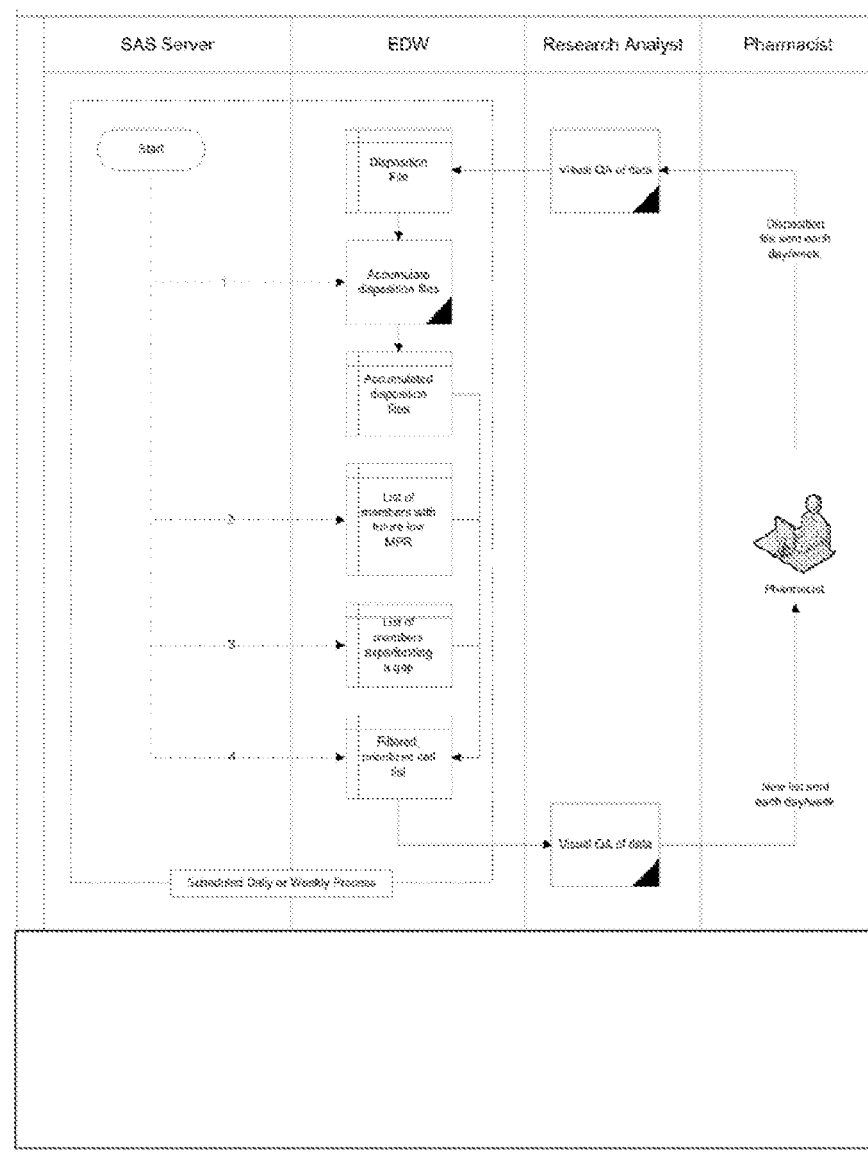
Figure 13C:
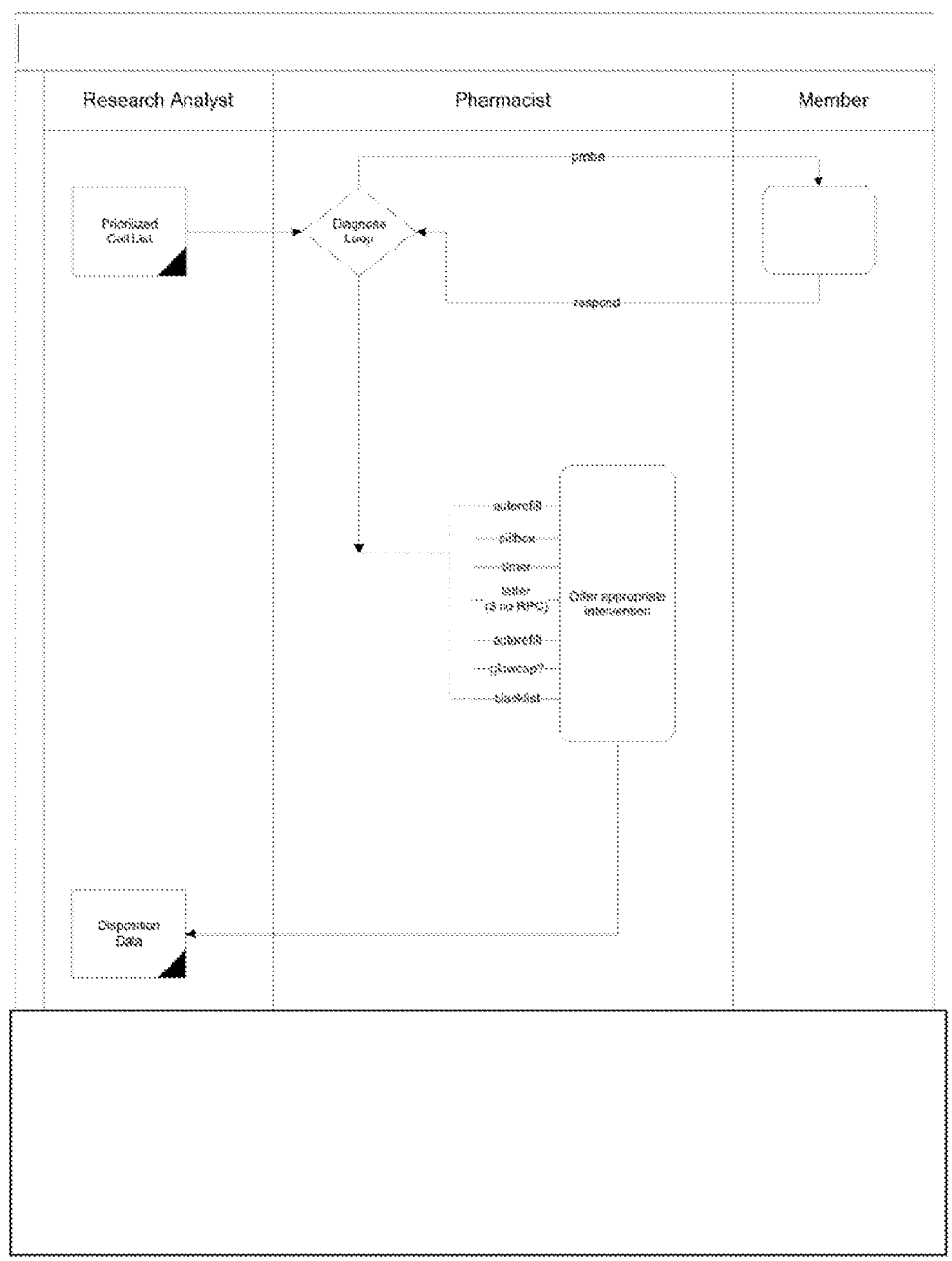

Referring to FIGS. 13A, 13B and 13C, a block diagram of the top level process flow is shown. The targeting process utilizes a basic member target list of those members who have been identified by the model as those who have not met a predefined adherence threshold. As members are contacted through the intervention process and program implementation has been identified, the contacted members may be added to a disposition list and the members may be removed from the basic target list. A cumulative disposition list may also be maintained over time. Continuously or periodically the disposition files may be accumulated and previously contacted members may be tracked to determine their adherence behavior. Based on the behavior found, a list of members having a low MPR may be determined and from that list a priority list may be determined filtered by the likelihood of success to improve adherence. During this tracking and evaluation process, the data may also be visually examined by research analyst and other experts like pharmacists. This may be used as a check to make sure that the predictions and data patterns that are detected add up in a logical manner. Expert consultants may also communicate with members in a manner designed to improve member adherence to therapy.

Figure 14A:
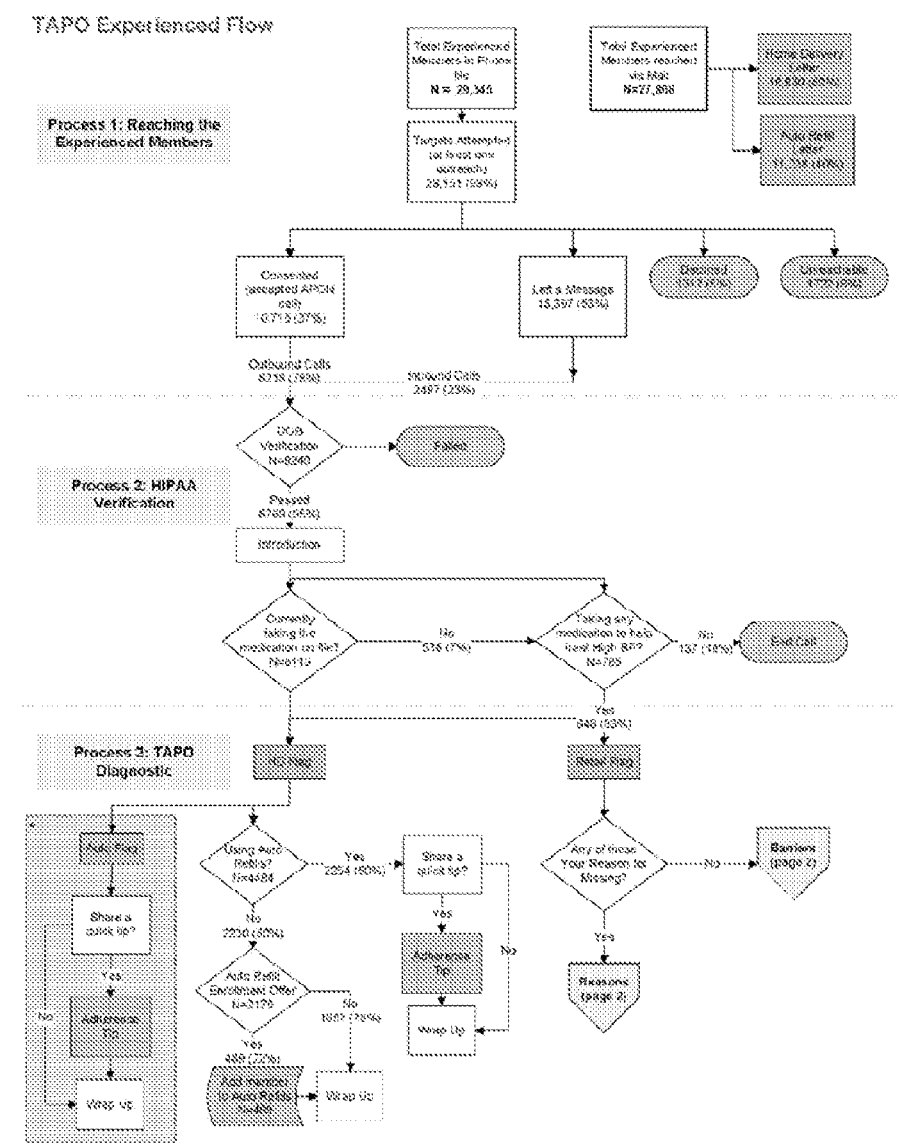
FIGS. 14A and 14B are a block diagram of the TAPO (Therapy Adherence Proactive Outreach) Experience flow for an experienced member, according to an example embodiment.
Figure 14B:
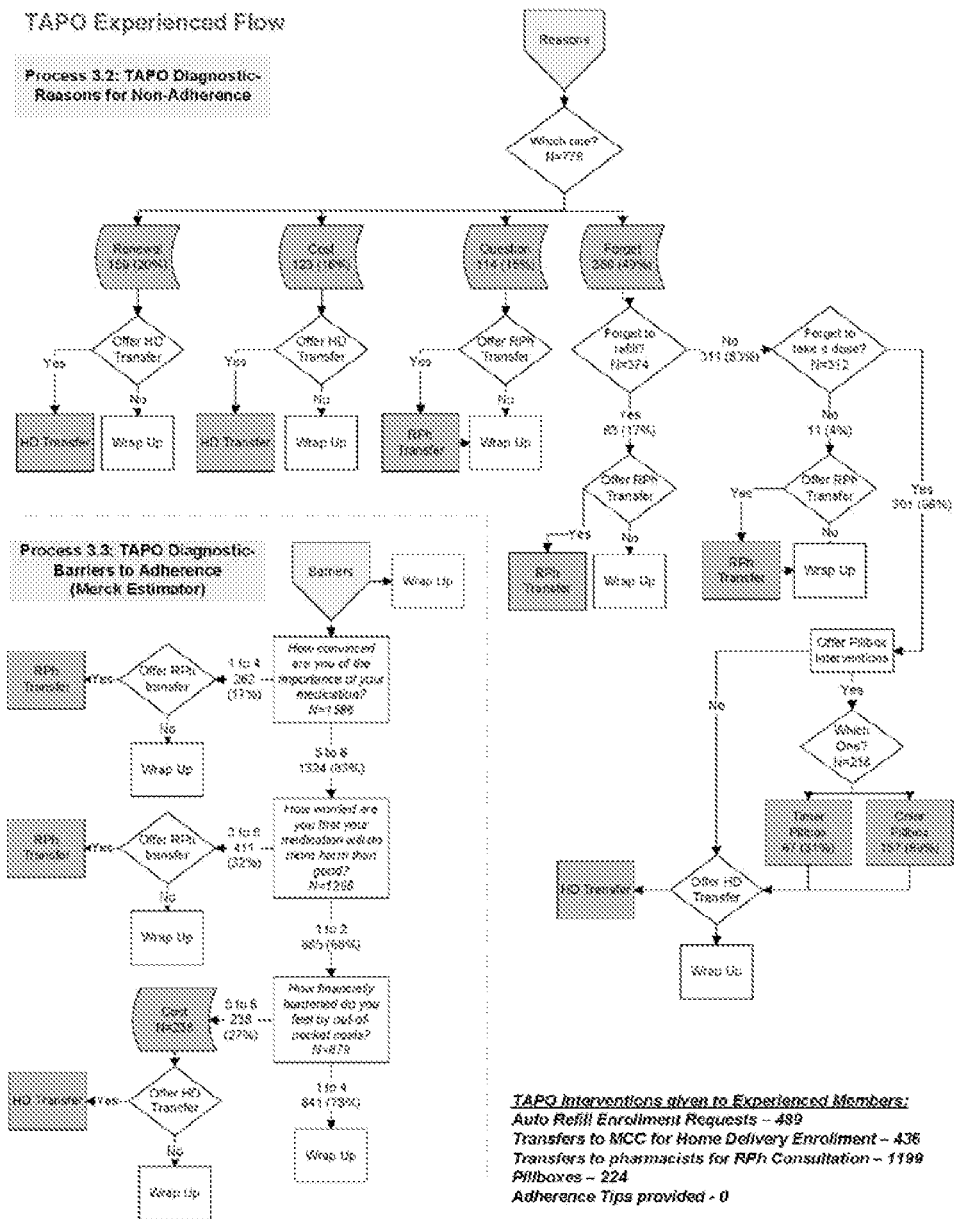
Figure 15A:
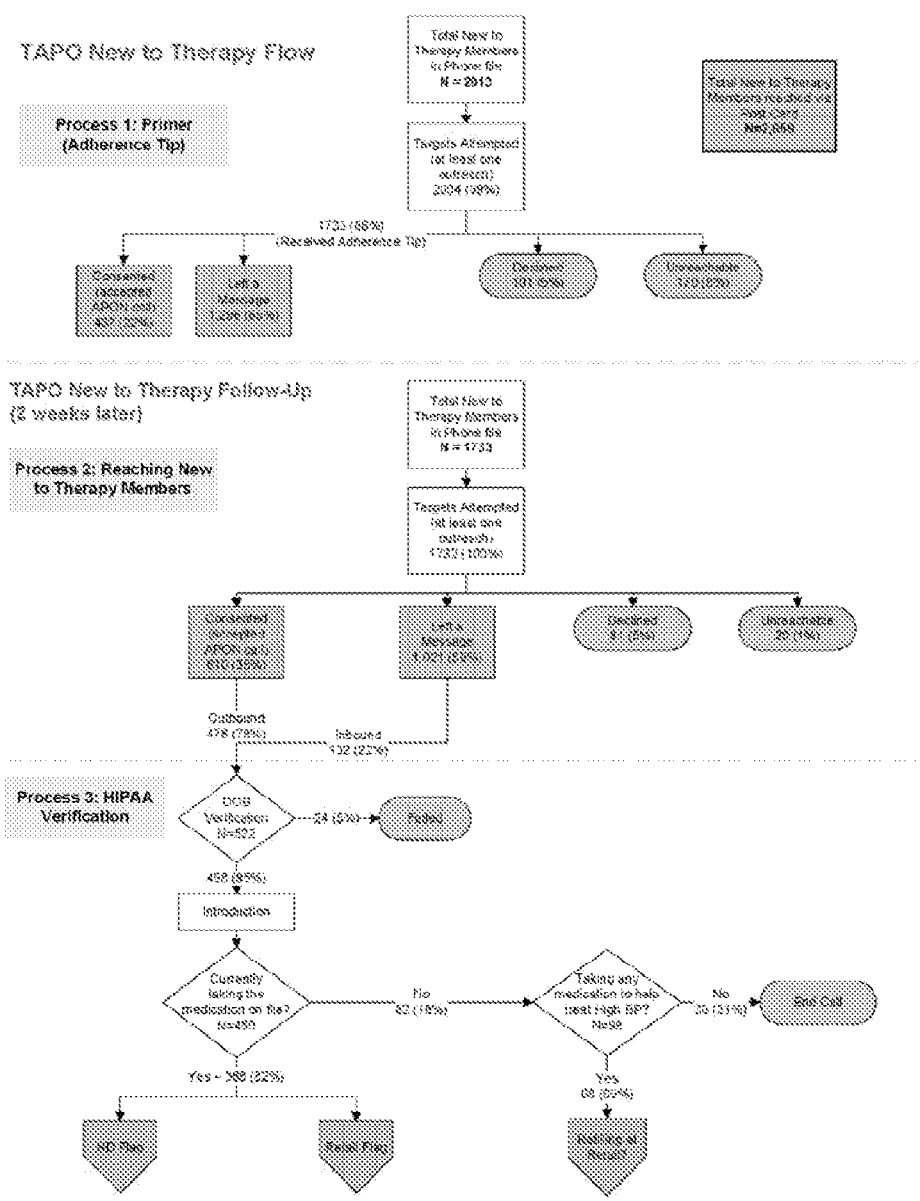
FIGS. 15A and 15B are a block diagram of the TAPO Experience flow for a new member, according to an example embodiment.
Figure 15B:
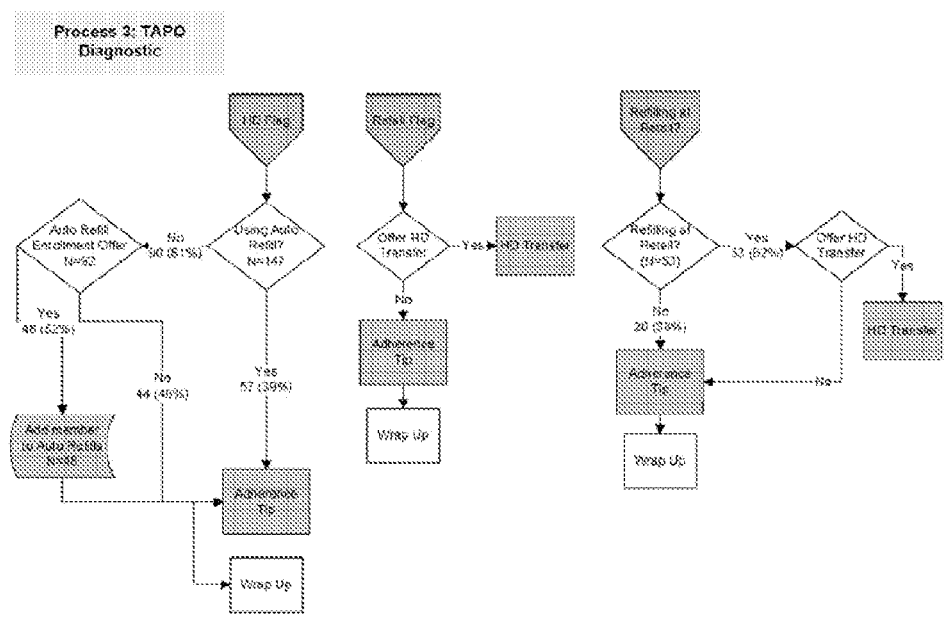
Figure 16A:
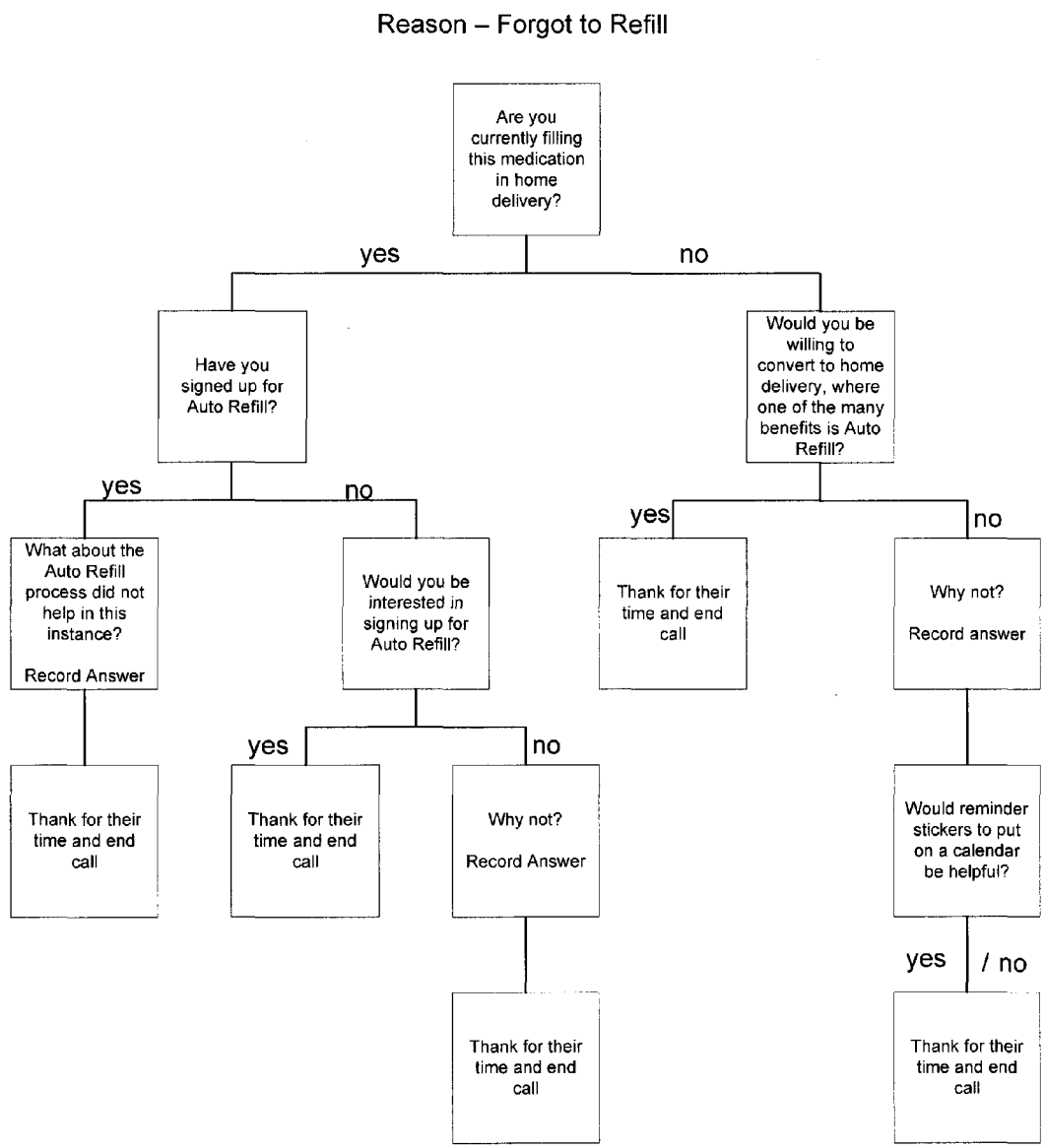
FIGS. 16A, 16B, 16C, 16D and 16E are a block diagram of a basic script for the TAPO Experience, according to an example embodiment.
Figure 16B:
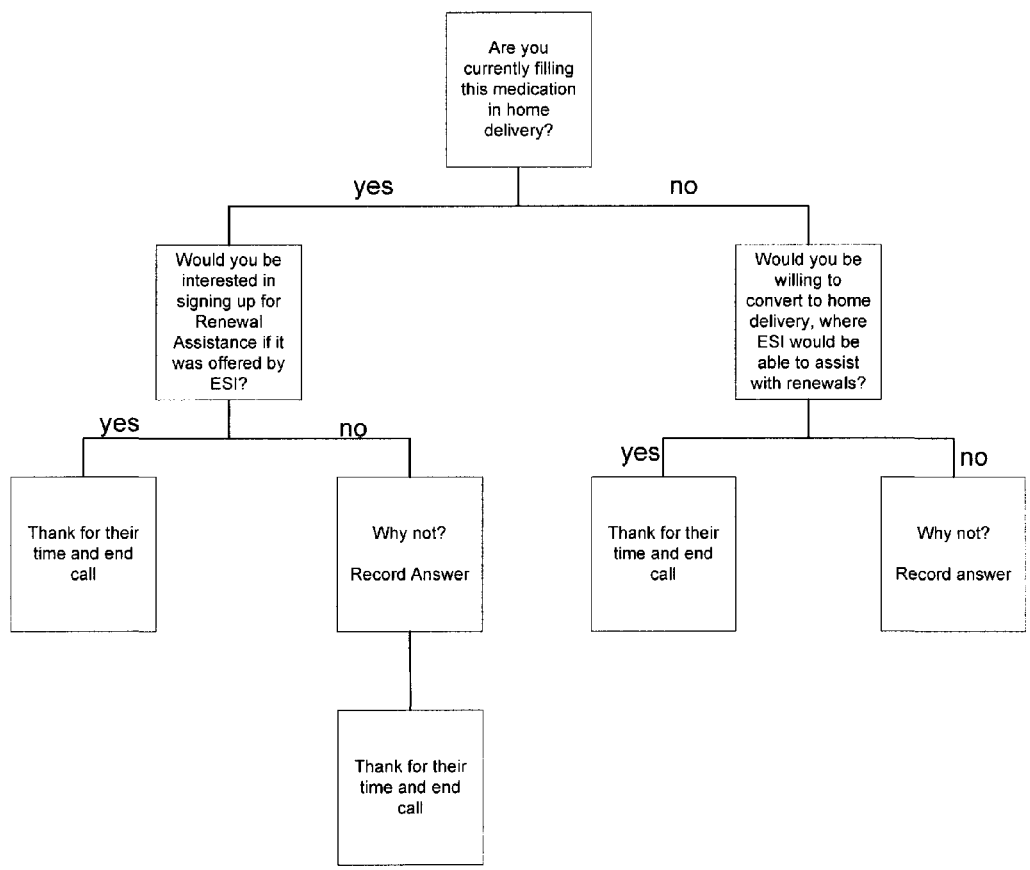
Figure 16C:
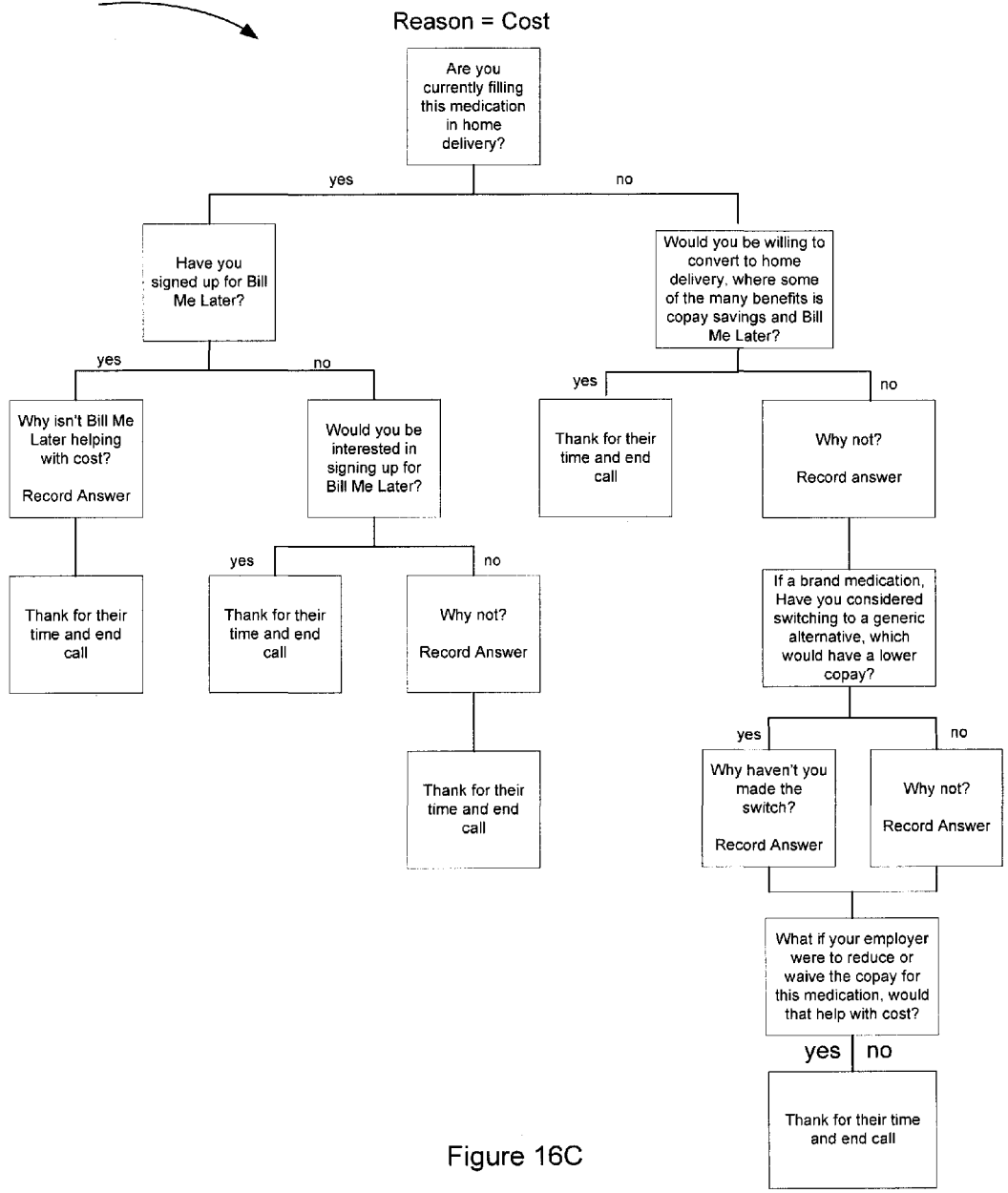
Figure 16D:
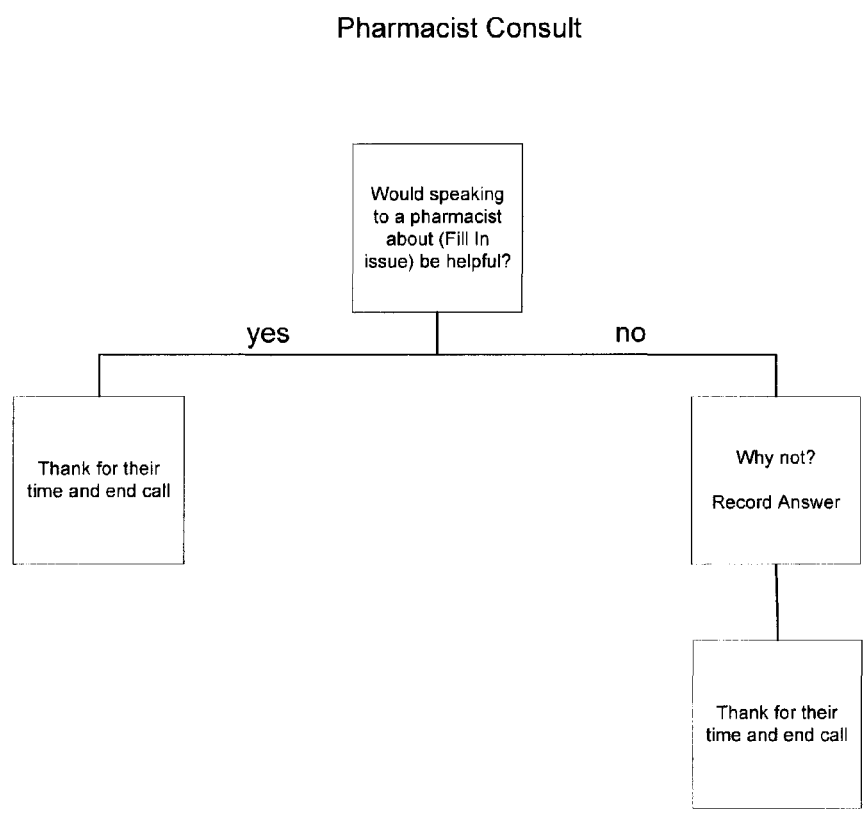
Figure 16E:
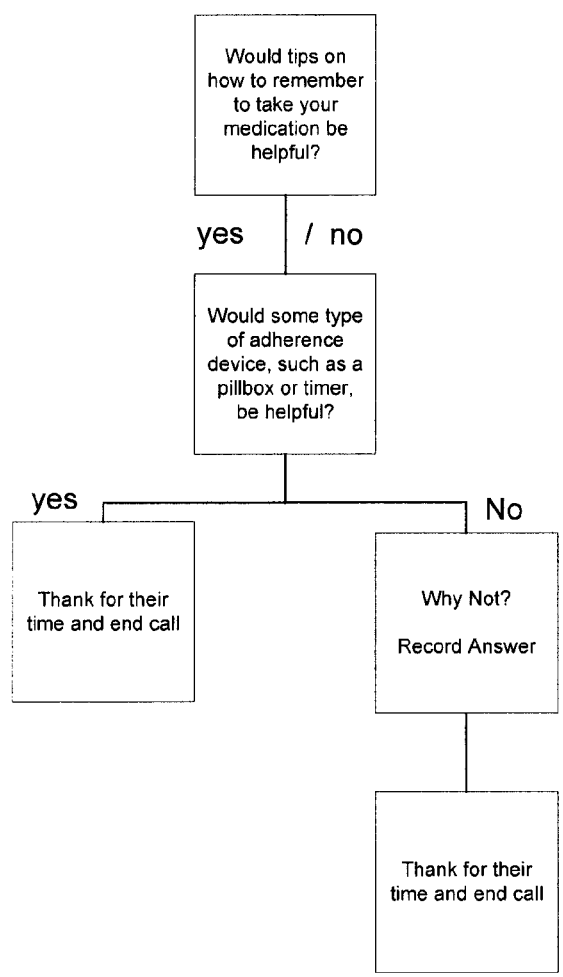

Referring to FIGS. 14A, 14B, 15A and 15B, a block diagram of an example TAPO (Therapy Adherence Proactive Outreach) experience flow for an experienced member and for a new member is shown. The new member script logic tree and the experienced member logic tree is just one example of how the logic trees that drive TAPO may be segregated, however, this is in no way limiting as the logic trees may be segregated by disease state and type of drug therapy. In addition, an embodiment may combine the multiple trees in to one logic tree with significantly large major branches. The model may predict at-risk members that will have a greater likelihood of not adhering to drug therapy and may be targeted for an outreach contact and the likely barrier to adherence may also be determined and intervention at the individual member level should be accomplished. The predictive modeling is a driver for TAPO to determine what intervention is decided. FIGS. 14A and 14B illustrates the TAPO flow for an experienced member and FIGS. 15A and 15B is for a new member.

An outreach may be attempted with the experienced member. A letter may be sent offering home delivery and auto refill. Telephone calls may also be attempted. If a member is reached by telephone, certain demographic questions may be asked of the member to obtain more specific individual demographics. A diagnostic may also be performed after certain inquiries are posed to the member. If poor adherence is determined, reasons for lack of adherence may be sought. A diagnostic may be performed to determine the barriers to adherence. Interventions may be determined based on the information gathered from the member. A similar process is provided for a new member.

As discussed above, communications with members before and/or after identified therapy adherence improvement program has been selected may be facilitated at the consultant communication device 106 as shown in FIGS. 1 and 5. For example, a patient consultant may use the consultant communication device 106 to facilitate communications with a member to gather data points for the member data 112 stored in the database 110 that may be used to determine the likelihood of therapy adherence by the member. After a therapy program has been identified for a particular member, the consultant communication device 106 may be used to implement or aid in implementing the therapy program.

For example, the consultant communication device 106 may generate communications to a member, may be used to offer home delivery to a member (and/or enroll a member in home delivery), and the like. The member may also have computing or personal digital assistant devices for receiving messages and other communications to improve adherence. Also special applications may be utilized on computing or personal digital assistant devices for management of medications and reminders. The consultant communication device 106 may include a member communication subsystem 502, as shown in FIG. 5. The consultant communication device 106 with the member communication subsystem 502 may be deployed in the system 100, or may be deployed in another system.

In one embodiment, a TAPO method may include the communication subsystem 502 accessing a target member list that is a list of individuals targeted for outreach by the member communication subsystem 502. The list may be generated using a predictive model that may predict which members will likely respond positively to such an outreach or may be determined by the MPR of the member.

Another embodiment may generate a list based on a selected group without utilizing a predictive model. The member communication subsystem 502 may provide a user interface to a human administrator, which prompts the administrator to reach out to a member, for example by telephone call, and further prompts the administrator with scripted questions and responses based on a script logic tree. The administrator may also be prompted with user interface fields for entry of member responses to questions, which may be stored to a database. The member responses may trigger execution of different portions of the script logic tree. In one embodiment the script logic tree may be comprehensive to include multiple disease states and multiple drug therapies. Another embodiment could utilize multiple script logic trees segregated by disease state, drug therapy or demographics. In either case the disease state and/or drug therapy may affect the flow of the script logic whether within the same logic tree or switching to a different logic tree.

In one embodiment, the predictive model may determine where the script begins within the logic tree or may eliminate portions of or entire branches of the logic tree. Background demographic data may also determine where the script begins within the logic tree or may eliminate portions of or entire branches of the logic tree. Once a diagnosis and recommended intervention is determined by member communication subsystem 502, the script logic tree will direct a recommendation or tip to the member. Another embodiment utilizes an automated telephone calling system that communicates with a member using computer generated scripting and a voice recognition engine. Therefore, rather than prompting an administrator with a user interface to ask certain questions, computer generated voice script is utilized; and rather than utilizing administrator inputs to member response fields on the user interface, the voice recognition engine interprets and logs the responses of the member.

The dialogue with the member facilitated by the TAPO method is designed to be a diagnostic tool to identify a need or a problem or a potential problem with the client that has contributed to or may contribute to non-adherence; and is designed to make suggestions to help address the need or problem in order to improve adherence. In one embodiment, the member response may determine the path within the logic tree and the ultimate intervention recommended. However, in another embodiment the intervention that is ultimately recommended may be impacted by the predictive models, MPR and/or the demographics of the member or group. Once suggestions or tips are made or changes in services are made the member adherence continues to be tracked by the system and the information gleaned and generated by TAPO may be correlated to later adherence numbers. This tracking and correlation may be utilized as feedback to the predictive model. In another embodiment, the dialogue with the member created by TAPO may be implemented via Email, a website browser environment, or text messaging.

In one embodiment the outreach may take on the form of an initial welcome to a member new to therapy as follows:
Outbound Call:
Hello, this is Express Scripts, the company chosen to manage your prescription-drug benefit, calling for <first name> <last name>.
Target Response: Yes or no, is this <he/she>?
If Target Response Is Yes: Great! This call may be recorded for quality assurance.—Then Go-To Introduction portion of logic tree; and then the Wrap-Up portion of tree
If Target Response is NO: Then can Go-To Unavailable portion of tree, which can utilize either and message designed for an answering machine or a message with a human.

In one embodiment the outreach may take on the form of two calls to a member new to therapy where the first call is brief and may provide a tip and the second call is more in depth and more of a diagnostic and provides program offers as follows:
The first part of the outreach can be similar to that of an initial welcome script. If the member or Target is reached and ID verification script can be initiated where date of birth and other relevant information such as customer numbers, policy numbers and plan numbers can be confirmed. If ID is confirmed, the drug therapy can be confirmed and a brief introduction can be provided. The member can then be prompted with questions to determine if retail or home delivery is being used by the member to obtain drugs. If retail is being used, then home delivery can be offered and an auto-refill plan can be offered. Also, a quick tips can be provided to the member. The method also can allow for inbound calls from the member to be accepted and after a similar verification and/or by using caller ID verification. When a call is accepted, a similar script can be initiated.

Similar introductions and verifications may be utilized for experienced members, however, more diagnostics may be performed and more information regarding the member and their adherence behavior may be gathered. FIGS. 14, 15 and 16 provide further information regarding the process flow within the logic tree.

Referring to FIGS. 16A, 16B, 16C, 16D and 16E, a block diagram of a basic script for the TAPO experience is shown. The flow diagrams show a representative TAPO script for various different reasons for non-adherence and how a communicative intervention with a member may attempt to get the member back on track. In one representative script, during the intervention with the member, an auto refill offering is made. Another is representative of a script were the underlying reason is a renewal for a maintenance medication is overdue and a home delivery program offering is made to the member. Another script is representative where the cost of the medication is the issue and home delivery is offered to bring down the cost and another alternative is offered as a bill me later program alternative. A pharmacist consultant contact is also represented and a scenario where forgetting is the reason for non-adherence and various reminder devices are offered to the member as a potential program to improve member adherence.

Figure 17:
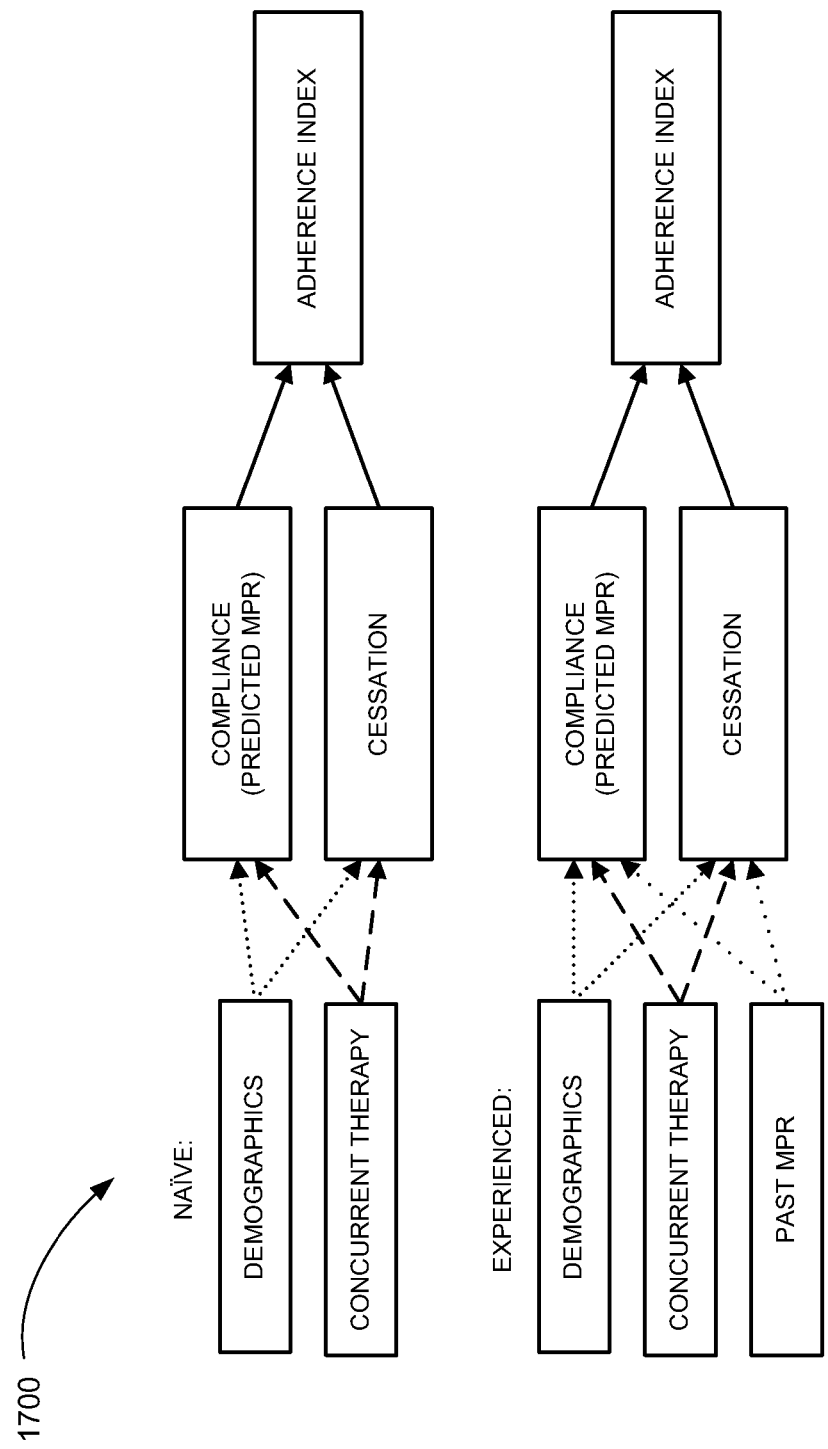
FIG. 17 is a block diagram of an adherence model, according to an example embodiment.

Referring to FIG. 17, as discussed herein the adherence prediction model may be separated into two components, a naive (new) member component and an experienced (continuous) member component. Each of the components may perform a statistical analysis of the demographic data and concurrent therapy data. Further, each component of the module may include a compliance module and a cessation module. In either case, a predicted MPR may be calculated based on the demographics. The predicted MPR may be factored in to refine the compliance module. Once actual demographic and actual past MPR data has been gathered and actual past MPR may be factored in with the demographics and concurrent therapy in the case of the experienced member component. As more and more data is gathered this actual past MPR factor may continue to refine the model. Further, as actual data is gathered a future MPR may be predicted and potentially utilized to factor in with the compliance module.

Therefore, there may be four underlying models and they are the new member predicted MPR refined compliance model, the new member cessation model, the experienced member predicted MPR refined compliance model and the experience member cessation model. These underlying models may be further refined based on type of disease or type of medication therapy and the associated behavioral data, which may correlate to a particular set of characteristics for why people may not be adherent.

For example, behavior data may reflect what appears to be a totally obscure factor that appears to have nothing to do with the disease state, but shows up as a statistically significant event and is repeatable and may be validated. The present invention may also factor in this statistically significant event.

Further the validation of the model and the statistically significant event is a continuous refinement. The model may capture patterns of behavior that may be related to disease type or medication therapy or other factor and may extract things that are common. If a pattern is identified as statistically significant, then that is going to be one of the factors that use to do the prediction for future compliance.

In an example embodiment, a member is targeted a based on an adherence index calculation. The targeted member may be contacted via a member interface and prompted with a humanly interpretable communication system, for example TAPO, which may include demographic questions, drug therapy questions, lack of adherence questions and offerings of alternative new programs to assist in adherence. The member may respond to the prompt and the response may be run through a diagnostic model and real time adherence tips may be communicated to the member via the member interface with humanly interpretable tip communications. Demographic response data from the member, drug therapy response data and lack of adherence response data may be stored a database and utilized to update the models.

Future member adherence behavior while under new program offering may be tracked if member affirmatively responds and accepts the alternative program offering. The future member behavior may be captured and stored in a database. A consultant may be contacted via a consultant interface and the consultant may be prompted with a humanly interpretable communication, which requests the consultant send a member adherence assistance communication to the member via member interface.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different embodiments of which there are many possible permutations.

In an implementation, a method for member messaging includes identifying disease state associated with a member; determining a member classification of the member, wherein the member classification is based on past therapy the member received to treat a condition associated with the disease state; selecting a diagnostic loop based on the disease state associated with the member and the member classification, wherein the diagnostic loop includes a plurality of operations; and performing least one of the plurality of operations of the diagnostic loop.

In an implementation, a method for member messaging includes identifying a member associated with a disease state using targeting data; determining a member classification of the member, wherein the member classification is based on past therapy the identified member received to treat a condition associated with the disease state; determining a probability of adherence to a prescription drug based on the identification of the member, the member classification, and the disease state associated with the member; and selecting an intervention from a plurality of interventions for the identified member based on the probability of adherence.

In an implementation, a system may include a processor; a memory coupled to the processor; a disease state identification module deployed in the memory and executed by the processor to identify a disease state associated with a member; a member classification module deployed in the memory and executed by the processor to determine a member classification of the member, wherein the member classification is based on past therapy the member received to treat a condition associated with the disease state; a therapy selection module deployed in the memory and executed by the processor to select a diagnostic loop based on the disease state associated with the member and the member classification, wherein the diagnostic loop includes a plurality of operations; and a therapy outreach module deployed in the memory and executed by the processor to perform at least one of the plurality of operations of the diagnostic loop.

In an implementation, a non-transitory machine-readable medium comprising instructions, which when executed by one or more processors, cause the one or more processors to perform the following operations: identifying, on a computer processor, a disease state associated with a member; determining, on the computer processor, a member classification of the member, wherein the member classification is based on past therapy the member received to treat a condition associated with the disease state; selecting, on the computer processor, a diagnostic loop based on the disease state associated with the member and the member classification, wherein the diagnostic loop includes a plurality of operations; and performing, on the computer processor, at least one of the plurality of operations of the diagnostic loop.

Thus, methods and systems for improving therapy adherence have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
    identifying, on a computer processor, a disease state associated with a member;
    determining, on the computer processor, a member classification of the member, wherein the member classification is based on past therapy the member received to treat a condition and whether the member is as a new-to-therapy member classification or an experienced-therapy member classification;
    selecting, on the computer processor, a diagnostic loop based on the disease state associated with the member and the member classification, wherein the diagnostic loop includes a plurality of operations that include a drug therapy operation related to a drug; and
    performing, on the computer processor, at least one of the plurality of operations of the diagnostic loop.

2. The method of claim 1, wherein performing the at least one of the plurality of operations includes:
    transmitting therapy adherence information and a therapy adherence offer to the member using the member classification,
    wherein the therapy adherence information includes information to improve adherence of the member to a prescription drug and the therapy adherence offer includes an offer to improve adherence of the member to the prescription drug.

3. The method of claim 2, wherein performing the at least one of the plurality of operations further comprises:
    identifying the prescription drug associated with the member, the prescription drug prescribed to treat a condition associated with the disease state;
    determining the member is taking the prescription drug as prescribed; and
    determining a pharmaceutical delivery channel associated with the prescription drug in response to determining the member is taking the prescription drug as prescribed,
    wherein transmitting the therapy adherence information and the therapy adherence offer to the member is in response to determining the member is taking the prescription drug as prescribed and determining the pharmaceutical delivery channel.

4. The method of claim 3, wherein the pharmaceutical delivery channel is a retail pharmacy and the therapy adherence offer includes an offer to switch from the retail pharmacy to a mail order pharmacy.

5. The method of claim 4, wherein the offer to switch from the retail pharmacy to the mail order pharmacy includes a prescription drug switch offer to switch a different prescription drug of the member from the retail pharmacy to the mail order pharmacy.

6. The method of claim 5, wherein the offer to switch from the retail pharmacy to the mail order pharmacy includes a care coordinator offer to connect the member to a care coordinator to transition the different prescription drug of the member from the retail pharmacy to the mail order pharmacy.

7. The method of claim 3, wherein the pharmaceutical delivery channel is a mail order pharmacy and the therapy adherence offer includes an offer to automatically refill the prescription drug through the mail order pharmacy.

8. The method of claim 1, wherein performing the at least one of the plurality of operations of the diagnostic loop further comprises:
    identifying a prescription drug associated with the member, the prescription drug prescribed to treat a condition associated with the disease state; and
    determining the member is not taking the prescription drug as prescribed.

9. The method of claim 8, further comprising:
    transmitting a not-taking-as-prescribed request, the not-taking-as-prescribed request
    including a request for information describing why the member is not taking the prescription drug as prescribed in response to the determination that the member is not taking the prescription drug as prescribed; and
    receiving a not-taking-as-prescribed response to the not-taking-as-prescribed request.

10. The method of claim 9, further comprising:
    transmitting an offer to switch from a retail pharmacy to a mail order pharmacy in response to receipt of the not-taking-as-prescribed response, wherein the response indicates one of the member forgot to renew the prescription drug, the member cannot afford the prescription drug, and the member forgot to refill the prescription drug; and transferring the member to a care coordinator in response to receiving the not-taking-as-prescribed response, wherein the not-taking-as-prescribed response indicates the member has a question regarding the prescription drug, the member forgot to take the prescription drug, or both.

11. The method of claim 9, further comprising:
determining that the member forgot to take a dose of the prescription drug using the received not-taking-as-prescribed response; and
transmitting a pillbox offer to the member in response to determining that the member forgot to take a dose of the prescription drug.

12. The method of claim 11, further comprising:
receiving a pillbox offer rejection response; and
transmitting an offer to switch from the retail pharmacy to a mail order pharmacy in response to receiving the pillbox offer rejection response.

13. The method of claim 1, further comprising:
accessing pharmacy claims data associated with the member;
determining the member is refilling a different prescription drug at a retail pharmacy based on the pharmacy claims data associated with the member; and
transmitting an offer to switch from the retail pharmacy to a mail order pharmacy in response to a determination that the member is refilling the different prescription drug.

14. A method comprising:
identifying, on a computer processor, a member associated with a disease state using targeting data;
determining, on the computer processor, a member classification of the member, wherein the member classification is based on past therapy the identified member received to treat a condition associated with the disease state and whether the identified member is a new-to-therapy member or an experienced-therapy member;
determining, on the computer processor, a probability of adherence to a prescription drug based on the identification of the member, the member classification, and the disease state associated with the member; and
selecting, on the computer processor, an intervention from a plurality of interventions for the identified member based on the probability of adherence.

15. The method of claim 14, further comprising:
accessing clinical data associated with the identified member;
determining the identified member has received a past therapy to treat a condition associated with the disease state; and
adjusting the selected intervention in response to determining the identified member has received a past therapy.

16. The method of claim 14, further comprising:
selecting a diagnostic loop based on the disease state associated with the identified member and the member classification, wherein the diagnostic loop includes a plurality of operations; and
performing at least one of the plurality of operations of the diagnostic loop, wherein the plurality of operations includes transmitting therapy adherence information and a therapy adherence offer to the identified member, wherein the therapy adherence information includes information to improve adherence of the member to a prescription drug and the therapy adherence offer includes an offer to improve adherence of the identified member to the prescription drug.

17. The method of claim 16, wherein performing the at least one of the plurality of operations of the diagnostic loop further comprises:
providing the selected intervention to the identified member,
wherein the selected intervention includes one or more of a postal mail message, an electronic mail message, a text message, a transfer from automated messaging to a personal representative, a refill pill box, an auto-refill of the prescription drug, and a late payment plan.

18. The method of claim 14, wherein the probability of adherence of the identified member to the prescription drug is based on the age of the identified member, the gender of the identified member, the disease state associated with the identified member, and the member classification of the identified member.

19. The method of claim 14, wherein determining the probability of adherence comprises:
determining a probability of therapy cessation based on demographic data of the
identified member and the disease state associated with the identified member;
determining a probability of therapy compliance based on demographic data of the identified member and the disease state associated with the identified member; and
calculating the probability of adherence of the identified member to the prescription drug based on the probability of therapy cessation and the probability of therapy compliance.

20. The method of claim 14, further comprising:
arranging a member health screening based on the determination of the intervention.

21. A system comprising:
a processor and a memory coupled to the processor;
a disease state identification module deployed in the memory and executed by the processor to identify a disease state associated with a member;
a member classification module deployed in the memory and executed by the processor to determine a member classification of the member, wherein the member classification is based on past therapy the member received to treat a condition associated with the disease state and whether the identified member is a new-to-therapy member or an experienced-therapy member;
a therapy selection module deployed in the memory and executed by the processor to select a diagnostic loop based on the disease state associated with the member and the member classification, wherein the diagnostic loop includes a plurality of operations; and
a therapy outreach module deployed in the memory and executed by the processor to perform at least one of the plurality of operations of the diagnostic loop.

22. A non-transitory machine-readable medium comprising instructions, which when executed by one or more processors, cause the one or more processors to perform the following operations:
identifying, on a computer processor, a disease state associated with a member;
determining, on the computer processor, a member classification of the member, wherein the member classification is based on past therapy the member received to treat a condition associated with the disease state and whether the identified member is a new-to-therapy member or an experienced-therapy member;

selecting, on the computer processor, a diagnostic loop based on the disease state associated with the member and the member classification, wherein the diagnostic loop includes a plurality of operations; and performing, on the computer processor, at least one of the plurality of operations of the diagnostic loop.

23. The medium of claim 22, further comprising:

accessing clinical data associated with the identified member;

determining the identified member has received a past therapy to treat a condition associated with the disease state;

adjusting the selected intervention in response to determining the identified member has received a past therapy;

selecting a diagnostic loop based on the disease state associated with the identified member and the member classification, wherein the diagnostic loop includes a plurality of operations; and performing at least one of the plurality of operations of the diagnostic loop, wherein the plurality of operations includes transmitting therapy adherence information and a therapy adherence offer to the identified member, wherein the therapy adherence information includes information to improve adherence of the member to a prescription drug and the therapy adherence offer includes an offer to improve adherence of the identified member to the prescription drug.

24. The medium of claim 23, wherein performing the at least one of the plurality of operations of the diagnostic loop further comprises:

providing the selected intervention to the identified member, wherein the selected intervention includes one or more of a postal mail message, an electronic mail message, a text message, a transfer from automated messaging to a personal representative, a refill pill box, an auto-refill of the prescription drug, and a late payment plan.

25. The medium of claim 22, wherein performing the at least one of the plurality of operations of the diagnostic loop includes determining a probability of adherence of the identified member to the prescription drug is based on the age of the identified member, the gender of the identified member, the disease state associated with the identified member, and the member classification of the identified member.

26. The medium of claim 22, wherein performing the at least one of the plurality of operations of the diagnostic loop includes comprises:

determining a probability of therapy cessation based on demographic data of the identified member and the disease state associated with the identified member;

determining a probability of therapy compliance based on demographic data of the identified member and the disease state associated with the identified member; and calculating the probability of adherence of the identified member to the prescription drug based on the probability of therapy cessation and the probability of therapy compliance.

27. The method of claim 1, wherein performing, on the computer processor, at least one of the plurality of operations of the diagnostic loop includes selecting a first loop when the member has a new-to-therapy member classification and selecting a second diagnostic loop when the member has an experienced-therapy member classification, wherein the second diagnostic loop is different than the first diagnostic loop and includes past medication possession ratio as a factor.

\* \* \* \* \*